United States Patent
Andrews et al.

(10) Patent No.: US 9,566,193 B2
(45) Date of Patent: Feb. 14, 2017

(54) METHODS AND APPARATUS FOR FORMING DISPOSABLE PRODUCTS AT HIGH SPEEDS WITH SMALL MACHINE FOOTPRINT

(75) Inventors: Robert E. Andrews, Sheboygan, WI (US); Jeffrey W. Fritz, Plymouth, WI (US); Gottfried Jason Hohm, Sheboygan Falls, WI (US); Adam D. DeNoble, De Pere, WI (US); Tyler W. Pagel, Grafton, WI (US); Christopher A. Schwartz, Sheboygan Falls, WI (US); Christopher J. Nelson, Plymouth, WI (US); Darren R. Horness, Sheboygan, WI (US); Alan J. Rabe, Howards Grove, WI (US); Sean P. Follen, Sheboygan Falls, WI (US); Brian G. Jankuski, Glenbeulah, WI (US)

(73) Assignee: Curt G. Joa, Inc., Sheboygan Falls, WI (US)

(*) Notice: Subject to any disclaimer, the term of this patent is extended or adjusted under 35 U.S.C. 154(b) by 232 days.

(21) Appl. No.: 13/404,905

(22) Filed: Feb. 24, 2012

(65) Prior Publication Data

US 2013/0056576 A1 Mar. 7, 2013

Related U.S. Application Data

(60) Provisional application No. 61/446,537, filed on Feb. 25, 2011.

(51) Int. Cl.
*A61F 13/15* (2006.01)

(52) U.S. Cl.
CPC ... *A61F 13/15577* (2013.01); *A61F 13/15699* (2013.01); *A61F 13/15723* (2013.01); *A61F 13/15764* (2013.01)

(58) Field of Classification Search
CPC .................. A61F 13/15577; A61F 13/15764; A61F 13/15723; A61F 13/15699
(Continued)

(56) References Cited

U.S. PATENT DOCUMENTS

| 135,145 | A | 1/1873 | Murphy |
| 293,353 | A | 2/1884 | Purvis |

(Continued)

FOREIGN PATENT DOCUMENTS

| BE | 1007854 | 11/1995 |
| CA | 1146129 | 5/1983 |

(Continued)

OTHER PUBLICATIONS

"Reciprocating Mechanisms", Franklin Jones, vol. 1, date unknown, 2 pages.

(Continued)

*Primary Examiner* — Emmanuel M Marcelo
*Assistant Examiner* — Michael Gallion
(74) *Attorney, Agent, or Firm* — Ryan Kromholz & Manion, S.C.

(57) ABSTRACT

The present invention provides machinery used to create products (for instance disposable products). The machinery is operated at high speed, with the machine occupying a small footprint. Materials can be fed into the manufacturing process vertically (from above or below), using assembly stations to feed completed components into the system at appropriate stations. Additionally, restocking of raw components can be accomplished by robotic means of transferring the raw material from staging areas into infeeding or splicing stations, without the need for human operators.

8 Claims, 10 Drawing Sheets

(58) Field of Classification Search
USPC ..... 242/533, 533.8, 539, 559, 560; 414/277, 414/278, 279, 280, 282, 286, 911
See application file for complete search history.

(56) References Cited

U.S. PATENT DOCUMENTS

| | | | |
|---|---|---|---|
| 312,257 A | 2/1885 | Cotton et al. | |
| 410,123 A | 8/1889 | Stilwell | |
| 432,742 A | 7/1890 | Stanley | |
| 643,821 A | 2/1900 | Howlett | |
| 1,393,524 A | 10/1921 | Grupe | |
| 1,431,315 A | 10/1922 | Le Moine | |
| 1,605,842 A | 11/1926 | Jones | |
| 1,686,595 A | 10/1928 | Belluche | |
| 1,957,651 A | 5/1934 | Joa | |
| 2,009,857 A | 7/1935 | Potdevin | |
| 2,054,832 A | 9/1936 | Potdevin | |
| 2,117,432 A | 5/1938 | Linscott | |
| 2,128,746 A | 8/1938 | Joa | |
| 2,131,808 A | 10/1938 | Joa | |
| 2,164,408 A | 7/1939 | Joa | |
| 2,167,179 A | 7/1939 | Joa | |
| 2,171,741 A | 9/1939 | Cohn et al. | |
| 2,213,431 A | 9/1940 | Joa | |
| 2,254,290 A | 9/1941 | Joa | |
| 2,254,291 A | 9/1941 | Joa | |
| 2,282,477 A | 5/1942 | Joa | |
| 2,286,096 A | 6/1942 | Joa | |
| 2,296,931 A | 9/1942 | Joa | |
| 2,304,571 A | 12/1942 | Joa | |
| 2,324,930 A | 7/1943 | Joa | |
| 2,345,937 A | 4/1944 | Joa | |
| 2,466,240 A | 4/1949 | Joa | |
| 2,481,929 A | 9/1949 | Joa | |
| 2,510,229 A | 6/1950 | Joa | |
| 2,540,844 A | 2/1951 | Strauss | |
| 2,584,002 A | 1/1952 | Elser et al. | |
| 2,591,359 A | 4/1952 | Joa | |
| 2,618,816 A | 11/1952 | Joa | |
| 2,627,859 A | 2/1953 | Hargrave | |
| 2,695,025 A * | 11/1954 | Andrews .................. | 604/398 |
| 2,702,406 A | 2/1955 | Reed | |
| 2,721,554 A | 10/1955 | Joa | |
| 2,730,144 A | 1/1956 | Joa | |
| 2,772,611 A | 12/1956 | Heywood | |
| 2,780,253 A | 2/1957 | Joa | |
| 2,785,609 A | 3/1957 | Billeb | |
| 2,788,786 A | 4/1957 | Dexter | |
| 2,811,905 A | 11/1957 | Kennedy, Jr. | |
| 2,828,745 A | 4/1958 | Deutz | |
| 2,839,059 A | 6/1958 | Joa | |
| 2,842,169 A | 7/1958 | Joa | |
| 2,851,934 A | 9/1958 | Heywood | |
| 2,875,724 A | 3/1959 | Joa | |
| 2,890,700 A | 6/1959 | Lonberg-Holm | |
| 2,913,862 A | 11/1959 | Sabee | |
| 2,939,461 A | 6/1960 | Joa | |
| 2,939,646 A | 6/1960 | Stone | |
| 2,960,143 A | 11/1960 | Joa | |
| 2,990,081 A | 6/1961 | De Neui et al. | |
| 2,991,739 A | 7/1961 | Joa | |
| 3,016,207 A | 1/1962 | Comstock, III | |
| 3,016,582 A | 1/1962 | Joa | |
| 3,017,795 A | 1/1962 | Joa | |
| 3,020,687 A | 2/1962 | Joa | |
| 3,021,135 A | 2/1962 | Joa | |
| 3,024,957 A | 3/1962 | Pinto | |
| 3,053,427 A | 9/1962 | Wasserman | |
| 3,054,516 A | 9/1962 | Joa | |
| 3,069,982 A | 12/1962 | Heywood et al. | |
| 3,086,253 A | 4/1963 | Joa | |
| 3,087,689 A | 4/1963 | Heim | |
| 3,089,494 A | 5/1963 | Schwartz | |
| 3,091,408 A | 5/1963 | Schoeneman | |
| 3,114,994 A | 12/1963 | Joa | |
| 3,122,293 A | 2/1964 | Joa | |
| 3,128,206 A | 4/1964 | Dungler | |
| 3,203,419 A | 8/1965 | Joa | |
| 3,230,955 A | 1/1966 | Joa | |
| 3,268,954 A | 8/1966 | Joa | |
| 3,288,037 A | 11/1966 | Burnett | |
| 3,289,254 A | 12/1966 | Joa | |
| 3,291,131 A | 12/1966 | Joa | |
| 3,301,114 A | 1/1967 | Joa | |
| 3,306,546 A | 2/1967 | Ryan | |
| 3,318,608 A | 5/1967 | Smrekar | |
| 3,322,589 A | 5/1967 | Joa | |
| 3,336,847 A | 8/1967 | Johnson | |
| 3,342,184 A | 9/1967 | Joa | |
| 3,356,092 A | 12/1967 | Joa | |
| 3,360,103 A | 12/1967 | Joa | |
| 3,391,777 A | 7/1968 | Joa | |
| 3,454,442 A | 7/1969 | Heller, Jr. | |
| 3,460,775 A * | 8/1969 | Bassett ............... | B65H 19/1815 242/555.6 |
| 3,463,413 A | 8/1969 | Smith | |
| 3,470,848 A | 10/1969 | Dreher | |
| 3,484,275 A | 12/1969 | Lewicki, Jr. | |
| 3,502,322 A | 3/1970 | Cran | |
| 3,521,639 A | 7/1970 | Joa | |
| 3,526,563 A | 9/1970 | Schott, Jr. | |
| 3,538,551 A | 11/1970 | Joa | |
| 3,540,641 A | 11/1970 | Besnyo | |
| 3,575,170 A | 4/1971 | Clark | |
| 3,607,578 A | 9/1971 | Berg et al. | |
| 3,635,462 A | 1/1972 | Joa | |
| 3,655,143 A * | 4/1972 | Wallis ................ | B65H 19/1868 242/555.6 |
| 3,656,741 A | 4/1972 | Macke et al. | |
| 3,666,611 A | 5/1972 | Joa | |
| 3,673,021 A | 6/1972 | Joa | |
| 3,685,818 A | 8/1972 | Burger et al. | |
| 3,728,191 A | 4/1973 | Wierzba et al. | |
| 3,751,224 A | 8/1973 | Wackerle | |
| 3,758,102 A | 9/1973 | Munn et al. | |
| 3,772,120 A | 11/1973 | Radzins | |
| 3,776,798 A | 12/1973 | Milano | |
| 3,796,360 A | 3/1974 | Alexeff | |
| 3,810,344 A * | 5/1974 | Evans et al. .................... | 53/529 |
| 3,811,987 A | 5/1974 | Wilkinson et al. | |
| 3,816,210 A | 6/1974 | Aoko et al. | |
| 3,836,089 A * | 9/1974 | Riemersma ............ | B65H 19/14 226/189 |
| 3,847,710 A | 11/1974 | Blomqvist et al. | |
| 3,854,917 A | 12/1974 | McKinney et al. | |
| 3,883,389 A | 5/1975 | Schott, Jr. | |
| 3,888,400 A | 6/1975 | Wiig | |
| 3,901,238 A | 8/1975 | Geller et al. | |
| 3,903,768 A | 9/1975 | Amberg et al. | |
| 3,904,147 A | 9/1975 | Taitel et al. | |
| 3,918,698 A | 11/1975 | Coast | |
| 3,960,646 A | 6/1976 | Wiedamann | |
| 3,971,524 A * | 7/1976 | Nudinger ................. | A24C 5/20 156/504 |
| 3,988,194 A | 10/1976 | Babcock et al. | |
| 3,991,994 A | 11/1976 | Farish | |
| 4,002,005 A | 1/1977 | Mueller et al. | |
| 4,003,298 A | 1/1977 | Schott, Jr. | |
| 4,009,814 A | 3/1977 | Singh | |
| 4,009,815 A | 3/1977 | Ericson et al. | |
| 4,053,150 A | 10/1977 | Lane | |
| 4,056,919 A | 11/1977 | Hirsch | |
| 4,081,301 A | 3/1978 | Buell | |
| 4,090,516 A | 5/1978 | Schaar | |
| 4,094,319 A | 6/1978 | Joa | |
| 4,103,595 A * | 8/1978 | Corse ......................... | 493/362 |
| 4,106,974 A | 8/1978 | Hirsch | |
| 4,108,584 A | 8/1978 | Radzins et al. | |
| 4,136,535 A | 1/1979 | Audas | |
| 4,141,193 A * | 2/1979 | Joa ................... | 53/529 |
| 4,141,509 A | 2/1979 | Radzins | |
| 4,142,626 A | 3/1979 | Bradley | |
| 4,157,934 A | 6/1979 | Ryan et al. | |
| 4,165,666 A | 8/1979 | Johnson et al. | |

(56) References Cited

U.S. PATENT DOCUMENTS

| | | |
|---|---|---|
| 4,168,776 A | 9/1979 | Hoeboer |
| 4,171,239 A | 10/1979 | Hirsch et al. |
| 4,205,679 A | 6/1980 | Repke et al. |
| 4,208,230 A | 6/1980 | Magarian |
| 4,213,356 A | 7/1980 | Armitage |
| 4,215,827 A | 8/1980 | Roberts et al. |
| 4,222,533 A | 9/1980 | Pongracz |
| 4,223,822 A | 9/1980 | Clitheroe |
| 4,231,129 A | 11/1980 | Winch |
| 4,236,955 A | 12/1980 | Prittie |
| 4,275,510 A | 6/1981 | George |
| 4,284,454 A | 8/1981 | Joa |
| 4,307,800 A * | 12/1981 | Joa ................. 198/374 |
| 4,316,756 A * | 2/1982 | Wilson ............ 156/227 |
| 4,325,519 A | 4/1982 | McLean |
| 4,331,418 A * | 5/1982 | Klebe ............. 414/277 |
| 4,342,206 A | 8/1982 | Rommel |
| 4,364,787 A | 12/1982 | Radzins |
| 4,374,576 A | 2/1983 | Ryan |
| 4,379,008 A | 4/1983 | Gross et al. |
| 4,394,898 A | 7/1983 | Campbell |
| 4,411,721 A * | 10/1983 | Wishart ........... 156/73.1 |
| 4,452,597 A | 6/1984 | Achelpohl |
| 4,492,608 A | 1/1985 | Hirsch et al. |
| 4,501,098 A | 2/1985 | Gregory |
| 4,508,528 A | 4/1985 | Hirsch et al. |
| 4,522,853 A | 6/1985 | Szonn et al. |
| 4,528,798 A * | 7/1985 | Meier ............. B65H 5/24 242/528 |
| 4,543,152 A | 9/1985 | Nozaka |
| 4,544,109 A * | 10/1985 | Andreasson ........ B65H 16/06 242/559.2 |
| 4,551,191 A | 11/1985 | Kock et al. |
| 4,586,199 A | 5/1986 | Birring |
| 4,587,790 A * | 5/1986 | Muller ............ 53/118 |
| 4,589,945 A | 5/1986 | Polit |
| 4,603,800 A | 8/1986 | Focke et al. |
| 4,608,115 A | 8/1986 | Schroth et al. |
| 4,610,681 A | 9/1986 | Strohbeen et al. |
| 4,610,682 A | 9/1986 | Kopp |
| 4,614,076 A | 9/1986 | Rathemacher |
| 4,619,357 A | 10/1986 | Radzins et al. |
| 4,634,482 A | 1/1987 | Lammers |
| 4,641,381 A | 2/1987 | Heran et al. |
| 4,642,150 A | 2/1987 | Stemmler |
| 4,642,839 A | 2/1987 | Urban |
| 4,650,530 A | 3/1987 | Mahoney et al. |
| 4,663,220 A | 5/1987 | Wisneski et al. |
| 4,672,705 A | 6/1987 | Bors et al. |
| 4,675,016 A | 6/1987 | Meuli et al. |
| 4,675,062 A | 6/1987 | Instance |
| 4,675,068 A | 6/1987 | Lundmark |
| 4,686,136 A | 8/1987 | Homonoff et al. |
| 4,693,056 A | 9/1987 | Raszewski |
| 4,701,239 A | 10/1987 | Craig |
| 4,707,970 A * | 11/1987 | Labombarde et al. ........ 53/529 |
| 4,720,415 A | 1/1988 | Vander Wielen et al. |
| 4,723,698 A | 2/1988 | Schoonderbeek |
| 4,726,725 A * | 2/1988 | Baker et al. ................ 414/283 |
| 4,726,874 A | 2/1988 | Van Vliet |
| 4,726,876 A | 2/1988 | Tomsovic, Jr. |
| 4,743,241 A | 5/1988 | Igaue et al. |
| 4,751,997 A | 6/1988 | Hirsch |
| 4,753,429 A | 6/1988 | Irvine et al. |
| 4,756,141 A | 7/1988 | Hirsch et al. |
| 4,764,325 A | 8/1988 | Angstadt |
| 4,765,780 A | 8/1988 | Angstadt |
| 4,776,920 A | 10/1988 | Ryan |
| 4,777,513 A | 10/1988 | Nelson |
| 4,782,647 A | 11/1988 | Williams et al. |
| 4,785,986 A | 11/1988 | Daane et al. |
| 4,795,451 A | 1/1989 | Buckley |
| 4,795,510 A | 1/1989 | Wittrock et al. |
| 4,798,353 A | 1/1989 | Peugh |
| 4,801,345 A | 1/1989 | Dussaud et al. |
| 4,802,570 A | 2/1989 | Hirsch et al. |
| 4,840,609 A * | 6/1989 | Jones et al. .................. 493/28 |
| 4,845,964 A | 7/1989 | Bors et al. |
| 4,864,802 A | 9/1989 | D'Angelo |
| 4,873,813 A * | 10/1989 | Labombarde et al. ......... 53/438 |
| 4,880,102 A | 11/1989 | Indrebo |
| 4,888,231 A | 12/1989 | Angstadt |
| 4,892,536 A | 1/1990 | Des Marais et al. |
| 4,904,440 A | 2/1990 | Angstadt |
| 4,908,175 A | 3/1990 | Angstadt |
| 4,909,019 A | 3/1990 | Delacretaz et al. |
| 4,909,697 A * | 3/1990 | Bernard et al. ........ 414/331.04 |
| 4,915,767 A | 4/1990 | Rajala et al. |
| 4,917,746 A | 4/1990 | Kons |
| 4,925,520 A | 5/1990 | Beaudoin et al. |
| 4,927,322 A | 5/1990 | Schweizer et al. |
| 4,927,486 A | 5/1990 | Fattal et al. |
| 4,927,582 A | 5/1990 | Bryson |
| 4,937,887 A | 7/1990 | Schreiner |
| 4,963,072 A | 10/1990 | Miley et al. |
| 4,987,940 A * | 1/1991 | Straub et al. ................ 156/164 |
| 4,994,010 A | 2/1991 | Doderer-Winkler |
| 5,000,806 A | 3/1991 | Merkatoris et al. |
| 5,007,522 A * | 4/1991 | Focke et al. ............... 198/468.8 |
| 5,021,111 A | 6/1991 | Swenson |
| 5,025,910 A | 6/1991 | Lasure et al. |
| 5,045,039 A | 9/1991 | Bay |
| 5,062,597 A | 11/1991 | Martin et al. |
| 5,064,179 A | 11/1991 | Martin |
| 5,064,492 A | 11/1991 | Friesch |
| 5,080,741 A | 1/1992 | Nomura et al. |
| 5,094,658 A | 3/1992 | Smithe et al. |
| 5,096,532 A | 3/1992 | Neuwirth et al. |
| 5,108,017 A | 4/1992 | Adamski, Jr. et al. |
| 5,109,767 A | 5/1992 | Nyfeler et al. |
| 5,110,403 A | 5/1992 | Ehlert |
| 5,127,981 A | 7/1992 | Straub et al. |
| 5,131,525 A | 7/1992 | Musschoot |
| 5,131,901 A | 7/1992 | Moll |
| 5,133,511 A | 7/1992 | Mack |
| 5,147,487 A | 9/1992 | Nomura et al. |
| 5,163,594 A | 11/1992 | Meyer |
| 5,171,239 A | 12/1992 | Igaue et al. |
| 5,176,244 A | 1/1993 | Radzins et al. |
| 5,183,252 A | 2/1993 | Wolber et al. |
| 5,188,627 A | 2/1993 | Igaue et al. |
| 5,190,234 A | 3/1993 | Ezekiel |
| 5,195,684 A | 3/1993 | Radzins |
| 5,203,043 A | 4/1993 | Riedel |
| 5,212,002 A * | 5/1993 | Madrzak ............. B65H 19/102 242/556.1 |
| 5,213,645 A | 5/1993 | Nomura et al. |
| 5,222,422 A | 6/1993 | Benner, Jr. et al. |
| 5,223,069 A | 6/1993 | Tokuno et al. |
| 5,226,992 A | 7/1993 | Morman |
| 5,246,433 A | 9/1993 | Hasse et al. |
| 5,252,228 A | 10/1993 | Stokes |
| 5,267,933 A | 12/1993 | Precoma |
| 5,273,228 A | 12/1993 | Yoshida |
| 5,275,676 A | 1/1994 | Rooyakkers et al. |
| 5,308,345 A | 5/1994 | Herrin |
| 5,328,438 A | 7/1994 | Crowley |
| 5,340,424 A | 8/1994 | Matsushita |
| 5,368,893 A | 11/1994 | Sommer et al. |
| 5,383,988 A * | 1/1995 | Herrmann ......... A61F 13/15804 156/297 |
| 5,389,173 A | 2/1995 | Merkatoris et al. |
| 5,393,360 A | 2/1995 | Bridges et al. |
| 5,407,507 A | 4/1995 | Ball |
| 5,407,513 A | 4/1995 | Hayden et al. |
| 5,415,649 A | 5/1995 | Watanabe et al. |
| 5,421,924 A | 6/1995 | Ziegelhoffer et al. |
| 5,424,025 A | 6/1995 | Hanschen et al. |
| 5,429,576 A | 7/1995 | Doderer-Winkler |
| 5,435,802 A | 7/1995 | Kober |
| 5,449,353 A | 9/1995 | Watanabe et al. |
| 5,464,401 A | 11/1995 | Hasse et al. |
| 5,472,153 A * | 12/1995 | Crowley et al. ............ 242/420.3 |
| 5,486,253 A | 1/1996 | Otruba |

(56) References Cited

U.S. PATENT DOCUMENTS

| | | | |
|---|---|---|---|
| 5,494,622 A | 2/1996 | Heath et al. | |
| 5,500,075 A | 3/1996 | Herrmann | |
| 5,513,936 A * | 5/1996 | Dean | 414/273 |
| 5,516,392 A | 5/1996 | Bridges et al. | |
| 5,518,566 A | 5/1996 | Bridges et al. | |
| 5,525,175 A | 6/1996 | Blenke et al. | |
| 5,531,850 A | 7/1996 | Herrmann | |
| 5,540,647 A | 7/1996 | Weiermann et al. | |
| 5,545,275 A | 8/1996 | Herrin et al. | |
| 5,545,285 A | 8/1996 | Johnson | |
| 5,552,013 A | 9/1996 | Ehlert et al. | |
| 5,556,246 A * | 9/1996 | Broshi | B65G 1/0478 414/239 |
| 5,556,360 A | 9/1996 | Kober et al. | |
| 5,556,504 A | 9/1996 | Rajala et al. | |
| 5,560,793 A | 10/1996 | Ruscher et al. | |
| 5,575,187 A | 11/1996 | Dieterlen | |
| 5,582,497 A * | 12/1996 | Noguchi | B65G 1/0407 414/268 |
| 5,586,964 A | 12/1996 | Chase | |
| 5,602,747 A | 2/1997 | Rajala | |
| 5,603,794 A | 2/1997 | Thomas | |
| 5,624,420 A | 4/1997 | Bridges et al. | |
| 5,624,428 A | 4/1997 | Sauer | |
| 5,628,738 A | 5/1997 | Suekane | |
| 5,634,917 A | 6/1997 | Fujioka et al. | |
| 5,643,165 A | 7/1997 | Klekamp | |
| 5,643,396 A | 7/1997 | Rajala et al. | |
| 5,645,543 A | 7/1997 | Nomura et al. | |
| 5,659,229 A | 8/1997 | Rajala | |
| 5,660,657 A | 8/1997 | Rajala et al. | |
| 5,660,665 A | 8/1997 | Jalonen | |
| 5,683,376 A | 11/1997 | Kato et al. | |
| 5,683,531 A | 11/1997 | Roessler et al. | |
| RE35,687 E | 12/1997 | Igaue et al. | |
| 5,693,165 A | 12/1997 | Schmitz | |
| 5,699,653 A | 12/1997 | Hartman et al. | |
| 5,705,013 A | 1/1998 | Nease | |
| 5,707,470 A | 1/1998 | Rajala et al. | |
| 5,711,832 A | 1/1998 | Glaug et al. | |
| 5,725,518 A | 3/1998 | Coates | |
| 5,725,714 A | 3/1998 | Fujioka | |
| 5,743,994 A | 4/1998 | Roessler et al. | |
| 5,745,922 A | 5/1998 | Rajala et al. | |
| 5,746,869 A | 5/1998 | Hayden et al. | |
| 5,749,989 A | 5/1998 | Linman et al. | |
| 5,766,389 A | 6/1998 | Brandon et al. | |
| 5,788,797 A | 8/1998 | Herrin et al. | |
| 5,817,199 A | 10/1998 | Brennecke et al. | |
| 5,829,164 A | 11/1998 | Kotitschke | |
| 5,836,931 A | 11/1998 | Toyoda et al. | |
| 5,858,012 A | 1/1999 | Yamaki et al. | |
| 5,865,393 A | 2/1999 | Kreft et al. | |
| 5,868,727 A | 2/1999 | Barr et al. | |
| 5,868,899 A * | 2/1999 | Gundersen | A61F 13/15804 156/349 |
| 5,876,027 A | 3/1999 | Fukui et al. | |
| 5,876,792 A | 3/1999 | Caldwell | |
| 5,879,500 A | 3/1999 | Herrin et al. | |
| 5,881,964 A * | 3/1999 | Fujikura | B65H 19/1836 156/505 |
| 5,897,291 A * | 4/1999 | Gerwe et al. | 414/790.7 |
| 5,902,431 A | 5/1999 | Wilkinson et al. | |
| 5,932,039 A | 8/1999 | Popp et al. | |
| 5,938,193 A | 8/1999 | Bluemle et al. | |
| 5,964,390 A | 10/1999 | Boerresen et al. | |
| 5,964,970 A | 10/1999 | Woolwine et al. | |
| 6,022,443 A | 2/2000 | Rajala et al. | |
| 6,036,805 A | 3/2000 | McNichols | |
| 6,043,836 A | 3/2000 | Kerr et al. | |
| 6,050,517 A * | 4/2000 | Dobrescu | B65H 20/34 226/118.2 |
| 6,074,110 A | 6/2000 | Verlinden et al. | |
| 6,076,442 A | 6/2000 | Arterburn et al. | |
| 6,098,249 A | 8/2000 | Toney et al. | |
| 6,123,792 A | 9/2000 | Samida et al. | |
| 6,171,432 B1 | 1/2001 | Brisebois | |
| 6,183,576 B1 | 2/2001 | Couillard et al. | |
| 6,195,850 B1 | 3/2001 | Melbye | |
| 6,210,386 B1 | 4/2001 | Inoue | |
| 6,212,859 B1 | 4/2001 | Bielik, Jr. et al. | |
| 6,214,147 B1 | 4/2001 | Mortellite et al. | |
| 6,217,274 B1 * | 4/2001 | Svyatsky et al. | 414/405 |
| 6,250,048 B1 | 6/2001 | Linkiewicz | |
| 6,264,133 B1 * | 7/2001 | Herrmann | B65H 19/123 242/528 |
| 6,264,784 B1 * | 7/2001 | Menard | A61F 13/15699 156/164 |
| 6,276,421 B1 | 8/2001 | Valenti et al. | |
| 6,276,587 B1 | 8/2001 | Boerresen | |
| 6,284,081 B1 | 9/2001 | Vogt et al. | |
| 6,287,409 B1 | 9/2001 | Stephany | |
| 6,306,122 B1 | 10/2001 | Narawa et al. | |
| 6,309,336 B1 | 10/2001 | Muessig et al. | |
| 6,312,420 B1 | 11/2001 | Sasaki et al. | |
| 6,314,333 B1 | 11/2001 | Rajala et al. | |
| 6,315,022 B1 | 11/2001 | Herrin et al. | |
| 6,319,347 B1 | 11/2001 | Rajala | |
| 6,336,921 B1 | 1/2002 | Kato et al. | |
| 6,358,350 B1 | 3/2002 | Glaug et al. | |
| 6,369,291 B1 * | 4/2002 | Uchimoto et al. | 604/367 |
| 6,375,769 B1 | 4/2002 | Quereshi et al. | |
| 6,391,013 B1 | 5/2002 | Suzuki et al. | |
| 6,416,697 B1 | 7/2002 | Venturino et al. | |
| 6,431,038 B2 | 8/2002 | Couturier | |
| 6,440,246 B1 | 8/2002 | Vogt et al. | |
| 6,443,389 B1 | 9/2002 | Palone | |
| 6,446,795 B1 | 9/2002 | Allen et al. | |
| 6,473,669 B2 | 10/2002 | Rajala et al. | |
| 6,475,325 B1 | 11/2002 | Parrish et al. | |
| 6,478,786 B1 | 11/2002 | Glaug et al. | |
| 6,482,278 B1 | 11/2002 | McCabe et al. | |
| 6,494,244 B2 | 12/2002 | Parrish et al. | |
| 6,514,233 B1 | 2/2003 | Glaug | |
| 6,521,320 B2 | 2/2003 | McCabe et al. | |
| 6,523,595 B1 | 2/2003 | Milner et al. | |
| 6,524,423 B1 | 2/2003 | Hilt et al. | |
| 6,533,879 B2 | 3/2003 | Quereshi et al. | |
| 6,540,857 B1 | 4/2003 | Coenen et al. | |
| 6,547,909 B1 | 4/2003 | Butterworth | |
| 6,551,228 B1 | 4/2003 | Richards | |
| 6,551,430 B1 | 4/2003 | Glaug et al. | |
| 6,554,815 B1 | 4/2003 | Umebayashi | |
| 6,569,275 B1 | 5/2003 | Popp et al. | |
| 6,572,520 B2 | 6/2003 | Blumle | |
| 6,581,517 B1 | 6/2003 | Becker et al. | |
| 6,585,841 B1 | 7/2003 | Popp et al. | |
| 6,589,149 B1 | 7/2003 | VanEperen et al. | |
| 6,596,107 B2 | 7/2003 | Stopher | |
| 6,596,108 B2 | 7/2003 | McCabe | |
| 6,605,172 B1 | 8/2003 | Anderson et al. | |
| 6,605,173 B2 | 8/2003 | Glaug et al. | |
| 6,637,583 B1 * | 10/2003 | Andersson | B31B 1/58 198/400 |
| 6,648,122 B1 | 11/2003 | Hirsch et al. | |
| 6,649,010 B2 | 11/2003 | Parrish et al. | |
| 6,656,309 B1 | 12/2003 | Parker et al. | |
| 6,659,150 B1 | 12/2003 | Perkins et al. | |
| 6,659,991 B2 | 12/2003 | Suckane | |
| 6,675,552 B2 | 1/2004 | Kunz et al. | |
| 6,684,925 B2 | 2/2004 | Nagate et al. | |
| 6,685,130 B2 * | 2/2004 | Stauber et al. | 242/533.8 |
| 6,701,992 B1 * | 3/2004 | Pasquale | B65H 21/00 156/304.1 |
| 6,722,494 B2 | 4/2004 | Nakakado | |
| 6,730,189 B1 | 5/2004 | Franzmann | |
| 6,743,324 B2 | 6/2004 | Hargett et al. | |
| 6,750,466 B2 | 6/2004 | Guha et al. | |
| 6,758,109 B2 | 7/2004 | Nakakado | |
| 6,766,817 B2 | 7/2004 | da Silva | |
| 6,808,582 B2 | 10/2004 | Popp et al. | |
| D497,991 S | 11/2004 | Otsubo et al. | |
| 6,814,217 B2 | 11/2004 | Blumenthal et al. | |

(56) References Cited

U.S. PATENT DOCUMENTS

| | | | |
|---|---|---|---|
| 6,820,671 B2 | 11/2004 | Calvert | |
| 6,837,840 B2 | 1/2005 | Yonekawa et al. | |
| 6,840,616 B2 | 1/2005 | Summers | |
| 6,852,186 B1* | 2/2005 | Matsuda et al. | 156/230 |
| 6,875,202 B2 | 4/2005 | Kumasaka et al. | |
| 6,893,528 B2 | 5/2005 | Middelstadt et al. | |
| 6,913,718 B2 | 7/2005 | Ducker | |
| 6,918,404 B2 | 7/2005 | Dias da Silva | |
| 6,976,521 B2 | 12/2005 | Mlinar | |
| 6,978,486 B2 | 12/2005 | Zhou et al. | |
| 6,978,964 B2* | 12/2005 | Beccari | 242/559 |
| 7,017,820 B1 | 3/2006 | Brunner | |
| 7,045,031 B2 | 5/2006 | Popp et al. | |
| 7,066,586 B2 | 6/2006 | da Silva | |
| 7,077,393 B2 | 7/2006 | Ishida | |
| 7,130,710 B2 | 10/2006 | Popp et al. | |
| 7,172,666 B2 | 2/2007 | Groves et al. | |
| 7,195,684 B2 | 3/2007 | Satoh | |
| 7,201,345 B2 | 4/2007 | Werner | |
| 7,214,174 B2* | 5/2007 | Allen et al. | 493/418 |
| 7,214,287 B2 | 5/2007 | Shiomi | |
| 7,247,219 B2 | 7/2007 | O'Dowd | |
| 7,303,708 B2 | 12/2007 | Andrews et al. | |
| 7,350,740 B2* | 4/2008 | Benvenuti | B65H 19/126 242/555.1 |
| 7,380,213 B2 | 5/2008 | Pokorny et al. | |
| 7,398,870 B2 | 7/2008 | McCabe | |
| 7,441,579 B2* | 10/2008 | Adami | B65H 19/1852 156/159 |
| 7,449,084 B2 | 11/2008 | Nakakado | |
| 7,452,436 B2 | 11/2008 | Andrews | |
| 7,533,709 B2 | 5/2009 | Meyer | |
| 7,537,215 B2 | 5/2009 | Beaudoin et al. | |
| 7,587,966 B2 | 9/2009 | Nakakado et al. | |
| 7,618,513 B2 | 11/2009 | Meyer | |
| 7,638,014 B2 | 12/2009 | Coose et al. | |
| 7,640,962 B2 | 1/2010 | Meyer et al. | |
| 7,703,599 B2 | 4/2010 | Meyer | |
| 7,708,849 B2 | 5/2010 | McCabe | |
| 7,770,712 B2 | 8/2010 | McCabe | |
| 7,771,407 B2 | 8/2010 | Umebayashi | |
| 7,780,052 B2 | 8/2010 | McCabe | |
| 7,811,403 B2 | 10/2010 | Andrews | |
| 7,861,756 B2 | 1/2011 | Jenquin et al. | |
| 7,871,400 B2 | 1/2011 | Sablone et al. | |
| 7,909,956 B2 | 3/2011 | Coose et al. | |
| 7,975,584 B2 | 7/2011 | McCabe | |
| 7,987,964 B2 | 8/2011 | McCabe | |
| 8,007,484 B2 | 8/2011 | McCabe et al. | |
| 8,007,623 B2 | 8/2011 | Andrews | |
| 8,011,493 B2 | 9/2011 | Giuliani et al. | |
| 8,016,972 B2 | 9/2011 | Andrews et al. | |
| 2001/0012813 A1 | 8/2001 | Bluemle | |
| 2001/0017181 A1 | 8/2001 | Otruba et al. | |
| 2002/0046802 A1 | 4/2002 | Tachibana et al. | |
| 2002/0059013 A1 | 5/2002 | Rajala et al. | |
| 2002/0096241 A1 | 7/2002 | Instance | |
| 2002/0125105 A1 | 9/2002 | Nakakado | |
| 2002/0162776 A1 | 11/2002 | Hergeth | |
| 2003/0000620 A1 | 1/2003 | Herrin et al. | |
| 2003/0015209 A1 | 1/2003 | Gingras et al. | |
| 2003/0051802 A1 | 3/2003 | Hargett et al. | |
| 2003/0052148 A1 | 3/2003 | Rajala et al. | |
| 2003/0066585 A1 | 4/2003 | McCabe | |
| 2003/0083638 A1 | 5/2003 | Molee | |
| 2003/0084984 A1 | 5/2003 | Glaug et al. | |
| 2003/0089447 A1 | 5/2003 | Molee et al. | |
| 2003/0121614 A1 | 7/2003 | Tabor et al. | |
| 2003/0135189 A1 | 7/2003 | Umebayashi | |
| 2004/0007328 A1 | 1/2004 | Popp et al. | |
| 2004/0016500 A1 | 1/2004 | Tachibana et al. | |
| 2004/0044325 A1 | 3/2004 | Corneliusson | |
| 2004/0087425 A1 | 5/2004 | Ng et al. | |
| 2004/0112517 A1 | 6/2004 | Groves et al. | |
| 2004/0164482 A1 | 8/2004 | Edinger | |
| 2004/0182497 A1 | 9/2004 | Lowrey | |
| 2004/0228709 A1* | 11/2004 | Ueda | 414/279 |
| 2005/0000628 A1 | 1/2005 | Norrby | |
| 2005/0022476 A1 | 2/2005 | Hamer | |
| 2005/0077418 A1 | 4/2005 | Werner et al. | |
| 2005/0139713 A1* | 6/2005 | Weber et al. | 242/418.1 |
| 2005/0196538 A1 | 9/2005 | Sommer et al. | |
| 2005/0230056 A1 | 10/2005 | Meyer et al. | |
| 2005/0230449 A1 | 10/2005 | Meyer et al. | |
| 2005/0233881 A1 | 10/2005 | Meyer | |
| 2005/0234412 A1 | 10/2005 | Andrews et al. | |
| 2005/0257881 A1* | 11/2005 | Coose | A61F 13/15593 156/256 |
| 2005/0275148 A1 | 12/2005 | Beaudoin et al. | |
| 2006/0021300 A1 | 2/2006 | Tada et al. | |
| 2006/0099055 A1* | 5/2006 | Stefani | 414/277 |
| 2006/0137298 A1 | 6/2006 | Oshita et al. | |
| 2006/0224137 A1 | 10/2006 | McCabe et al. | |
| 2006/0265867 A1 | 11/2006 | Schaap | |
| 2007/0044895 A1* | 3/2007 | Nawano | B65H 19/1836 156/157 |
| 2007/0074953 A1 | 4/2007 | McCabe | |
| 2007/0131343 A1 | 6/2007 | Nordang | |
| 2007/0131817 A1 | 6/2007 | Fromm | |
| 2007/0140817 A1* | 6/2007 | Hansl | 414/277 |
| 2008/0223537 A1 | 9/2008 | Wiedmann | |
| 2009/0020211 A1 | 1/2009 | Andrews et al. | |
| 2010/0078119 A1 | 4/2010 | Yamamoto | |
| 2010/0078120 A1 | 4/2010 | Otsubo | |
| 2010/0078127 A1 | 4/2010 | Yamamoto | |
| 2010/0193138 A1 | 8/2010 | Eckstein | |
| 2010/0193155 A1 | 8/2010 | Nakatani | |
| 2011/0033270 A1* | 2/2011 | Toncelli | 414/277 |
| 2011/0041997 A1* | 2/2011 | Benner | A61F 13/15764 156/269 |
| 2012/0159753 A1* | 6/2012 | Andrews | A61F 13/15 26/70 |

FOREIGN PATENT DOCUMENTS

| | | |
|---|---|---|
| CA | 1153345 | 9/1983 |
| CA | 1190078 | 7/1985 |
| CA | 1210744 | 9/1986 |
| CA | 1212132 | 9/1986 |
| CA | 1236056 | 5/1988 |
| CA | 1249102 | 1/1989 |
| CA | 1292201 | 11/1991 |
| CA | 1307244 | 9/1992 |
| CA | 1308015 | 9/1992 |
| CA | 1310342 | 11/1992 |
| CA | 2023816 | 3/1994 |
| CA | 2404154 | 10/2001 |
| CA | 2541194 | 10/2006 |
| CA | 2559517 | 4/2007 |
| CA | 2337700 | 8/2008 |
| CA | 2407867 | 6/2010 |
| DE | 60123502 | 10/2006 |
| DE | 60216550 | 12/2006 |
| DE | 102005048868 | 4/2007 |
| DE | 102006047280 | 4/2007 |
| EP | 0044206 | 1/1982 |
| EP | 0048011 | 3/1982 |
| EP | 0089106 | 9/1983 |
| EP | 0099732 | 2/1984 |
| EP | 0206208 | 12/1986 |
| EP | 0304140 | 2/1989 |
| EP | 0439897 | 8/1991 |
| EP | 0455231 A1 | 11/1991 |
| EP | 510251 | 10/1992 |
| EP | 0652175 A1 | 5/1995 |
| EP | 0811473 | 12/1997 |
| EP | 0901780 | 3/1999 |
| EP | 0990588 | 4/2000 |
| EP | 1132325 A2 | 9/2001 |
| EP | 1199057 | 4/2002 |
| EP | 1272347 | 1/2003 |
| EP | 1366734 | 12/2003 |
| EP | 1571249 | 9/2005 |

(56) References Cited

FOREIGN PATENT DOCUMENTS

| | | |
|---|---|---|
| EP | 1619008 | 1/2006 |
| EP | 1707168 A2 | 10/2006 |
| EP | 1726414 | 11/2006 |
| EP | 1302424 | 12/2006 |
| EP | 1801045 | 6/2007 |
| EP | 1941853 | 7/2008 |
| EP | 1994919 | 11/2008 |
| EP | 2233116 | 9/2010 |
| EP | 2238955 | 10/2010 |
| ES | 509706 | 11/1982 |
| ES | 520559 | 12/1983 |
| ES | 296211 | 12/1987 |
| ES | 200601373 | 7/2009 |
| ES | 2311349 | 9/2009 |
| FR | 2177355 | 11/1973 |
| FR | 2255961 | 7/1975 |
| FR | 1132325 | 10/2006 |
| FR | 2891811 | 4/2007 |
| GB | 191101501 A | 0/1912 |
| GB | 439897 | 12/1935 |
| GB | 856389 | 12/1960 |
| GB | 941073 | 11/1963 |
| GB | 1096373 | 12/1967 |
| GB | 1126539 | 9/1968 |
| GB | 1346329 | 2/1974 |
| GB | 1412812 | 11/1975 |
| GB | 2045298 | 10/1980 |
| GB | 2115775 | 9/1983 |
| GB | 2288316 | 10/1995 |
| IT | 1374910 | 5/2010 |
| IT | 1374911 | 5/2010 |
| JP | 428364 | 1/1992 |
| JP | 542180 | 2/1993 |
| JP | 576566 | 3/1993 |
| JP | 626160 | 2/1994 |
| JP | 626161 | 2/1994 |
| JP | 6197925 A | 7/1994 |
| JP | 9299398 | 11/1997 |
| JP | 10035621 | 2/1998 |
| JP | 10-277091 A | 10/1998 |
| SE | 0602047 | 5/2007 |
| SE | 0601003-7 | 6/2007 |
| SE | 0601145-6 | 10/2009 |
| WO | WO9403301 | 2/1994 |
| WO | WO9732552 | 9/1997 |
| WO | WO9747265 | 12/1997 |
| WO | WO9747810 | 12/1997 |
| WO | WO9821134 | 5/1998 |
| WO | WO9907319 | 2/1999 |
| WO | WO9913813 A1 | 3/1999 |
| WO | WO9932385 | 7/1999 |
| WO | WO9965437 | 12/1999 |
| WO | WO0143682 | 6/2001 |
| WO | WO0172237 A2 | 10/2001 |
| WO | WO2004007329 | 1/2004 |
| WO | WO2005075163 | 8/2005 |
| WO | WO2007029115 | 3/2007 |
| WO | WO2007039800 | 4/2007 |
| WO | WO2007126347 | 11/2007 |
| WO | WO2008001209 | 1/2008 |
| WO | WO2008155618 | 12/2008 |

OTHER PUBLICATIONS

International Search Report dated Jul. 31, 2012 regarding EP Application No. 12157191.3, 5 pages.

* cited by examiner

METHODS AND APPARATUS FOR FORMING DISPOSABLE PRODUCTS AT HIGH SPEEDS WITH SMALL MACHINE FOOTPRINT

RELATED APPLICATIONS

This application claims the benefit of U.S. Provisional Patent Application Ser. No. 61/446,537, filed 25 Feb. 2011.

BACKGROUND OF THE INVENTION

The invention disclosed herein relates to an apparatus and methods for forming disposable products such as diapers at very high speeds, while significantly reducing the footprint of the machine, while also reducing waste. While the description provided relates to diaper manufacturing, the apparatus and method are easily adaptable to other applications.

Generally, diapers comprise an absorbent insert or patch and a chassis, which, when the diaper is worn, supports the insert proximate a wearer's body. Additionally, diapers may include other various patches, such as tape tab patches, reusable fasteners and the like. The raw materials used in forming a representative insert are typically cellulose pulp, tissue paper, poly, nonwoven web, acquisition, and elastic, although application specific materials are sometimes utilized. Usually, most of the insert raw materials are provided in roll form, and unwound and applied in continuously fed fashion.

In the creation of a diaper, multiple roll-fed web processes are typically utilized. To create an absorbent insert, the cellulose pulp is unwound from the provided raw material roll and de-bonded by a pulp mill. Discrete pulp cores are created using a vacuum forming assembly and placed on a continuous tissue web. Optionally, super-absorbent powder may be added to the pulp core. The tissue web is wrapped around the pulp core. The wrapped core is debulked by proceeding through a calender unit, which at least partially compresses the core, thereby increasing its density and structural integrity. After debulking, the tissue-wrapped core is passed through a segregation or knife unit, where individual wrapped cores are cut. The cut cores are conveyed, at the proper pitch, or spacing, to a boundary compression unit.

While the insert cores are being formed, other insert components are being prepared to be presented to the boundary compression unit. For instance, the poly sheet is prepared to receive a cut core. Like the cellulose pulp, poly sheet material is usually provided in roll form. The poly sheet is fed through a splicer and accumulator, coated with an adhesive in a predetermined pattern, and then presented to the boundary compression unit. In addition to the poly sheet, which may form the bottom of the insert, a two-ply top sheet may also be formed in parallel to the core formation. Representative plies are an acquisition layer web material and a nonwoven web material, both of which are fed from material parent rolls, through a splicer and accumulator. The plies are coated with adhesive, adhered together, cut to size, and presented to the boundary compression unit. Therefore, at the boundary compression unit, three components are provided for assembly: the poly bottom sheet, the core, and the two-ply top sheet.

A representative boundary compression unit includes a profiled die roller and a smooth platen roller. When all three insert components are provided to the boundary compression unit, the nip of the rollers properly compresses the boundary of the insert. Thus, provided at the output of the boundary compression unit is a string of interconnected diaper inserts. The diaper inserts are then separated by an insert knife assembly and properly oriented, such as disclosed in co-pending U.S. Application No. 61/426,891, owned by the assignee of the present invention and incorporated herein by reference. At this point, the completed insert is ready for placement on a diaper chassis.

A representative diaper chassis comprises nonwoven web material and support structure. The diaper support structure is generally elastic and may include leg elastic, waistband elastic and belly band elastic. The support structure is usually sandwiched between layers of the nonwoven web material, which is fed from material rolls, through splicers and accumulators. The chassis may also be provided with several patches, besides the absorbent insert. Representative patches include adhesive tape tabs and resealable closures.

The process utilizes two main carrier webs; a nonwoven web which forms an inner liner web, and an outer web that forms an outwardly facing layer in the finished diaper. In a representative chassis process, the nonwoven web is slit at a slitter station by rotary knives along three lines, thereby forming four webs. One of the lines is on approximately the centerline of the web and the other two lines are parallel to and spaced a short distance from the centerline. The effect of such slitting is twofold; first, to separate the nonwoven web into two inner diaper liners. One liner will become the inside of the front of the diaper, and the second liner will become the inside of the back of that garment. Second, two separate, relatively narrow strips are formed that may be subsequently used to cover and entrap portions of the leg-hole elastics. The strips can be separated physically by an angularly disposed spreader roll and aligned laterally with their downstream target positions on the inner edges of the formed liners. This is also done with turn bars upon entrance to the process.

After the nonwoven web is slit, an adhesive is applied to the liners in a predetermined pattern in preparation to receive leg-hole elastic. The leg-hole elastic is applied to the liners and then covered with the narrow strips previously separated from the nonwoven web. Adhesive is applied to the outer web, which is then combined with the assembled inner webs having elastic thereon, thereby forming the diaper chassis. Next, after the elastic members have been sandwiched between the inner and outer webs, an adhesive is applied to the chassis. The chassis is now ready to receive an insert.

In diapers it is preferable to contain elastics around the leg region in a cuff to contain exudates for securely within the diaper. Typically, strands of elastic are held by a non-woven layer that is folded over itself and contains the elastics within the overlap of the non-woven material. The non-woven is typically folded by use of a plow system which captures the elastics within a pocket, which is then sealed to ensure that the elastics remain in the cuff.

Most products require some longitudinal folding. It can be combined with elastic strands to make a cuff. It can be used to overwrap a stiff edge to soften the feel of the product. It can also be used to convert the final product into a smaller form to improve the packaging.

To assemble the final diaper product, the insert must be combined with the chassis. The placement of the insert onto the chassis occurs on a placement drum or at a patch applicator. The inserts are provided to the chassis on the placement drum at a desired pitch or spacing. The generally flat chassis/insert combination is then folded so that the inner webs face each other, and the combination is trimmed.

A sealer bonds the webs at appropriate locations prior to individual diapers being cut from the folded and sealed webs.

Roll-fed web processes typically use splicers and accumulators to assist in providing continuous webs during web processing operations. A first web is fed from a supply wheel (the expiring roll) into the manufacturing process. As the material from the expiring roll is depleted, it is necessary to splice the leading edge of a second web from a standby roll to the first web on the expiring roll in a manner that will not cause interruption of the web supply to a web consuming or utilizing device.

In a splicing system, a web accumulation dancer system may be employed, in which an accumulator collects a substantial length of the first web. By using an accumulator, the material being fed into the process can continue, yet the trailing end of the material can be stopped or slowed for a short time interval so that it can be spliced to leading edge of the new supply roll. The leading portion of the expiring roll remains supplied continuously to the web-utilizing device. The accumulator continues to feed the web utilization process while the expiring roll is stopped and the new web on a standby roll can be spliced to the end of the expiring roll.

In this manner, the device has a constant web supply being paid out from the accumulator, while the stopped web material in the accumulator can be spliced to the standby roll. Examples of web accumulators include that disclosed in U.S. patent application Ser. No. 11/110,616, which is commonly owned by the assignee of the present application, and incorporated herein by reference.

As in many manufacturing operations, waste minimization is a goal in web processing applications, as products having spliced raw materials cannot be sold to consumers. Indeed, due to the rate at which web processing machines run, even minimal waste can cause inefficiencies of scale. In present systems, waste materials are recycled. However, the act of harvesting recyclable materials from defective product is intensive. That is, recyclable materials are harvested only after an identification of a reject product at or near the end of a process. The result is that recyclable materials are commingled, and harvesting requires the extra step of separating waste components. Therefore, the art of web processing would benefit from systems and methods that identify potentially defective product prior to product assembly, thereby eliminating effort during recyclable material harvesting.

Furthermore, to improve quality and production levels by eliminating some potentially defective product, the art of web processing would benefit from systems and methods that ensure higher product yield and less machine downtime.

Some diaper forming techniques are disclosed in co-pending U.S. application Ser. No. 12/925,033 which is incorporated herein by reference. As described therein, a process wherein a rotary knife or die, with one or more cutting edges, turns against and in coordination with a corresponding cylinder to create preferably trapezoidal ears. Ear material is slit into two lanes, one for a left side of a diaper and the other for a right side of a diaper. Fastening tapes are applied to both the right and the left ear webs. The ear material is then die cut with a nested pattern on a synchronized vacuum anvil.

The resulting discrete ear pieces however, due to the trapezoidal pattern of the ears, alternate between a correct orientation and an incorrect (reversed) orientation. The reversed ear is required to be rotated 180° into the correct orientation such that the ears and associated tape present a left ear and a right ear on the diaper.

To accomplish the reversal of the ear pattern, discrete ear pieces are picked up at the nested ear pitch by an ear turner assembly that will expand to a pitch large enough for ears to be unnested and allow clearance for every other ear to be rotated. The rotated ears are then unnested and into the correct orientation.

Two ear turner assemblies can be provided, to rotate every other ear applied to the right side of the product, and every other ear applied to the left side of the product. In this manner, for a single product, one of the two ears will have been rotated 180°.

Ear application to a chassis web can be by a bump method (described later) with intermittent adhesive applied to the chassis web, or can be by vacuum transfer.

The present invention also allows for two side panel assemblies, including fastening mechanisms, to be attached to two ears, the side panel assemblies attached in a pre-folded condition. Two more ears can coupled to a chassis web to create a front panel to wear about the waist of a user.

The present invention also allows for chips of material to be removed from the ears to provide a diaper with contoured leg openings. In one embodiment, the chips may be removed from the ears before the ears are attached to the chassis web. In an additional embodiment the chips may be removed from the ears after the ears are attached to the chassis web. In an additional embodiment the chips may be removed from the ears and a portion of the chassis web removed after the ears are attached to the chassis web.

The invention disclosed herein also relates to apparatus and methods for waste reduction, such as disclosed in co-pending U.S. Application Ser. No. 61/400,318, also incorporated herein by reference. Generally, diapers comprise an absorbent insert or patch and a chassis, which, when the diaper is worn, supports the insert proximate a wearer's body. Additionally, diapers may include other various patches, such as tape tab patches, reusable fasteners and the like. The raw materials used in forming a representative insert are typically cellulose pulp, tissue paper, poly, nonwoven web, acquisition, and elastic, although application specific materials are sometimes utilized. Usually, most of the insert raw materials are provided in roll form, and unwound and applied in assembly line fashion. As in many manufacturing operations, waste minimization is a goal in web processing applications, as products having spliced raw materials cannot be sold to consumers. Indeed, due to the rate at which web processing machines run, even minimal waste can cause inefficiencies of scale.

In present systems, waste materials are recycled. However, the act of harvesting recyclable materials from defective product is intensive. That is, recyclable materials are harvested only after an identification of a reject product at or near the end of a process. The result is that recyclable materials are commingled, and harvesting requires the extra step of separating waste components. Therefore, it is beneficial to use up all of incoming rolls, so that a portion of the incoming rolls do not become waste. That objective is accomplished with the present invention When manufacturing hygiene products, such as baby diapers, adult diapers, disposable undergarments, incontinence devices, sanitary napkins and the like, a common method of applying discrete pieces of one web to another is by use of a slip-and-cut applicator. A slip-and-cut applicator is typically comprised of a cylindrical rotating vacuum anvil, a rotating knife roll, and a transfer device. In typical applications, an incoming web is fed at a relatively low speed along the vacuum face of the rotating anvil, which is moving at a relatively higher surface speed and upon which the incoming web is allowed to "slip". A knife-edge, mounted on the rotating knife roll, cuts a off a segment of the incoming web against the anvil face. This knife-edge is preferably moving at a surface velocity similar to that of the anvil's surface. Once cut, the web segment is held by vacuum drawn through holes on the anvil's face as it is carried at the anvil's speed downstream to the transfer point where the web segment is transferred to the traveling web.

Continual improvements and competitive pressures have incrementally increased the operational speeds of disposable diaper converters. As speeds increased, the mechanical integrity and operational capabilities of the applicators had to be improved accordingly.

Decreasing the footprint required by the manufacturing equipment is also desirable, as is increased automation, decreased system downtime, and increased manufacturing speeds. In typical disposable products manufacturing techniques, raw materials are fed into the manufacturing system at ground level, generally from the sides (and often perpendicular on the ground level) relative to the main machine direction on the ground.

The raw material supply system can also done manually. A forklift operator is typically required to constantly monitor supplies of raw materials, such as the non-woven materials, elastics, pulp, SAP, tape, poly, etc. and drive the forklift from a storage area containing these materials, and deposit those materials onto the system, where typically splicing systems are used to provide for continuous operation.

SUMMARY OF THE INVENTION

Provided are methods and apparatus for minimizing waste and improving quality and production in web processing operations in a high speed, small footprint environment. Materials can be fed into the manufacturing process vertically (from above or below), using assembly stations to feed completed components into the system at appropriate stations. Additionally, restocking of raw components can be accomplished by robotic means of transferring the raw material from staging areas into infeeding or splicing stations, without the need for human operators.

The present invention allows for square, and non-square, and preferably trapezoidal, ear webs to be applied to a traveling web, with zero or minimized waste present in the incoming ear web. Zero material is wasted due to the geometry of the chosen ear pattern and its downstream processing.

An ear is a component of a diaper that is grasped and pulled around the waist of a wearer. Typically, ears are secured to the diaper at a first end, and a second free end is typically equipped with securing means, such as a pressure sensitive adhesive, or hook and loop material. As a user grasps an ear and pulls the ear, elasticity provided about the waist region of the diaper allows the free end to be snugly pulled about the waist of a wearer, and coupled to the diaper. Ears can be rectangular or made of irregular shapes.

The present invention provides a process wherein a rotary knife or die, with one or more cutting edges, turns against and in coordination with a corresponding cylinder to create preferably trapezoidal ears. Ear material is slit into two lanes, one for a left side of a diaper and the other for a right side of a diaper. Fastening tapes are applied to both the right and the left ear webs. The ear material is then die cut with a nested pattern on a synchronized vacuum anvil.

The resulting discrete ear pieces however, due to the trapezoidal pattern of the ears, alternate between a correct orientation and an incorrect (reversed) orientation. The reversed ear is required to be rotated 180° into the correct orientation such that the ears and associated tape present a left ear and a right ear on the diaper.

To accomplish the reversal of the ear pattern, discrete ear pieces are picked up at the nested ear pitch by an ear turner assembly that will expand to a pitch large enough for ears to be unnested and allow clearance for every other ear to be rotated. The rotated ears are then unnested and into the correct orientation.

Two ear turner assemblies can be provided, to rotate every other ear applied to the right side of the product, and every other ear applied to the left side of the product. In this manner, for a single product, one of the two ears will have been rotated 180°.

Ear application to a chassis web can be by a bump method (described later) with intermittent adhesive applied to the chassis web, or can be by vacuum transfer.

The present invention also allows for two side panel assemblies, including fastening mechanisms, to be attached to two ears, the side panel assemblies attached in a pre-folded condition. Two more ears can coupled to a chassis web to create a front panel to wear about the waist of a user.

The present invention also allows for chips of material to be removed from the ears to provide a diaper with contoured leg openings. In one embodiment, the chips may be removed from the ears before the ears are attached to the chassis web. In an additional embodiment the chips may be removed from the ears after the ears are attached to the chassis web. In an additional embodiment the chips may be removed from the ears and a portion of the chassis web removed after the ears are attached to the chassis web.

One aspect of the present invention is a novel machine layout. Materials are unwound from either an automated or a manned mezzanine level, and materials are transported and unwound vertically, preferably to a ground floor, to be used in manufacture of either brief type or pant type disposable products. A significantly compact floor plan is achieved which reduces machine footprint from prior standards to less than eighty (80) and preferably less than sixty (60) foot lengths from start of processing to finishing of the disposable products.

A multi-level machine for manufacturing disposable products is disclosed, the machine comprising a material unwinding level carrying unmanned, auto-fed material unwinding systems carrying materials. The auto-fed material unwinding systems are operatively connected to and feed materials to a main processing level for use in manufacturing a disposable product.

A material staging magazine is provided to carry waiting new material rolls from a ground level to a mezzanine level, the mezzanine level carrying a series of turret unwind systems for dispensing materials from the mezzanine level back to the ground level for use in diaper manufacturing operations. The material staging magazines contain a series of individual roll stabilization features which prevent waiting new material rolls from tipping during material transport and unloading. Waiting new material rolls can include an inner non-woven material, an outer-non-woven material, a non-woven backsheet material, a non-woven topsheet material, a poly backsheet material, an acquisition layer material, and a tissue layer. The material staging magazine is loaded at the ground floor, transported to the unwind level, and then automatically transported roll-by-roll their respective unwind system for use in manufacturing the disposable products.

A vertical reciprocating conveyor or a robot is used to carry waiting new material rolls from the said main processing level to the material unwinding level. Once on the material unwinding level, the waiting new material rolls are staged at a material address dedicated to that particular material. A robotic assembly acquires a material roll from one of said material addresses and transports and places the material roll onto its appropriate auto-fed material unwinding system. The robotic assembly then obtains the expiring roll and discards the roll in a waste chute.

In another novel aspect of the present invention, a process interface module is provided vertically displaced between the unwind level and the main processing level, while the main level contains splice preparation equipment.

The material supply techniques and product layouts disclosed can be used to produce pant-type diapers, brief-type diapers, baby diapers, adult diapers, or any other types of disposable products using web processing machinery.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

It is noted that the present waste minimization techniques and apparatus are described herein with respect to products such as diapers, but as previously mentioned, can be applied to a wide variety of processes in which discrete components are applied sequentially.

Figure 1A:
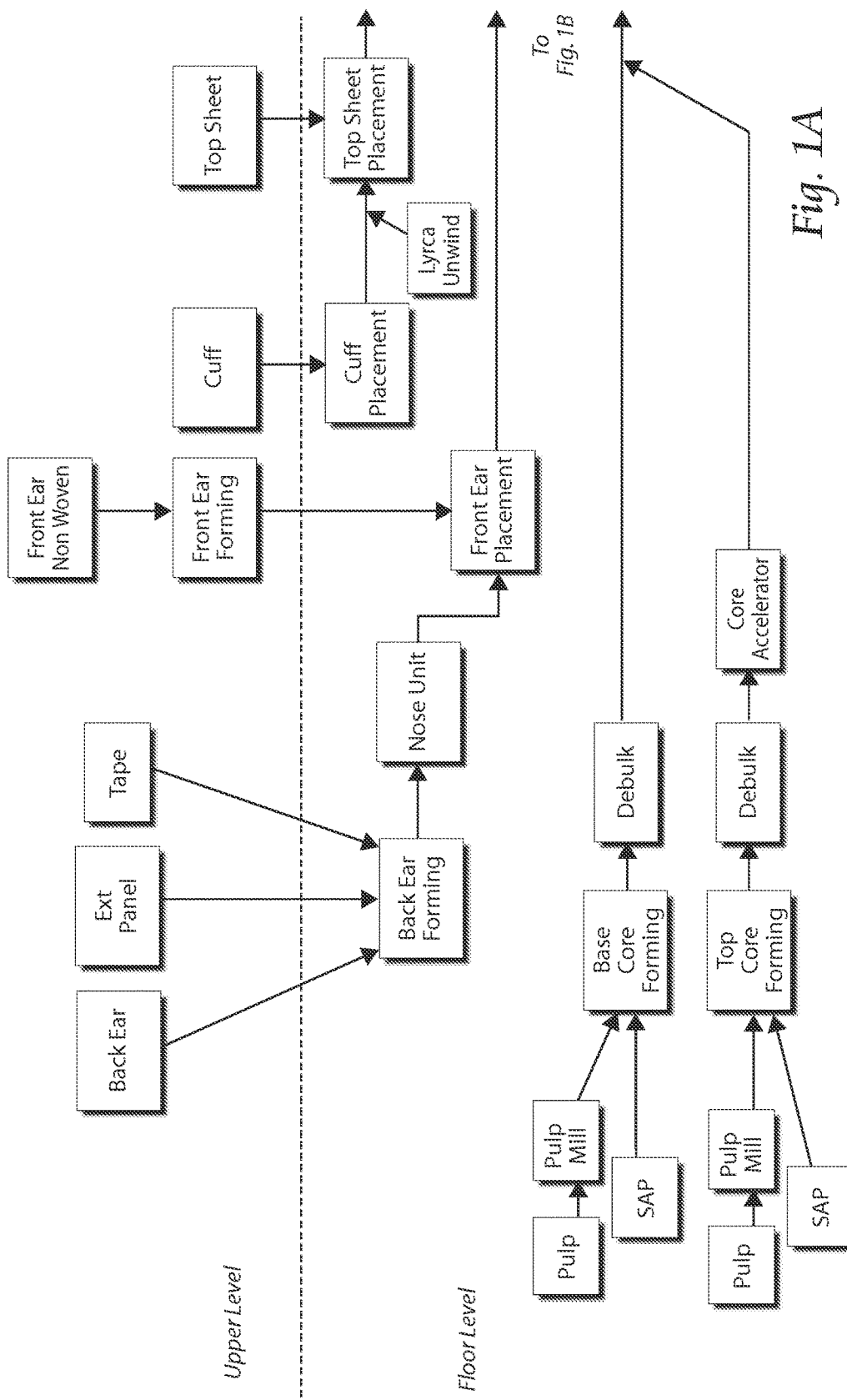
FIGS. 1A and 1B are a schematic of a representative web processing system.
Figure 1B:
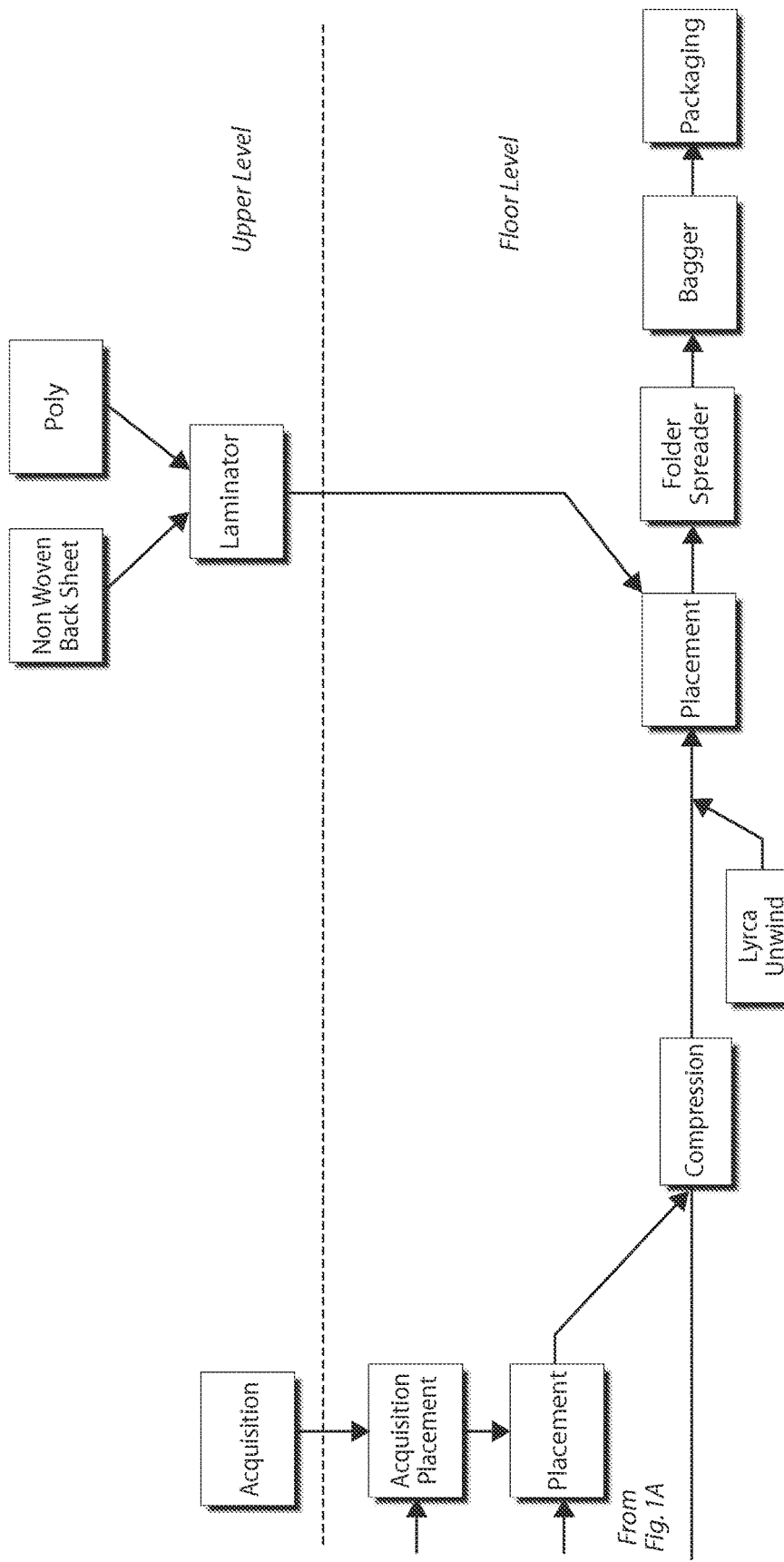

Referring to FIGS. 1A and 1B, a two-level disposable product manufacturing process is disclosed. Portions of the disposable product are formed on a floor level, and other portions are formed on an upper or mezzanine level.

On the floor level, the web processing operation starts with incorporating raw materials such as paper pulp and super absorbent polymer (SAP) in a pulp mill. The mixture is sent to a core forming drum, where cores are formed for retaining liquids. A core can be placed on a tissue and processed as shown. Eventually, an additional tissue layer can be applied to sandwich the core. In the illustrated embodiment, two independent cores can be formed and joined together at a compression unit.

Simultaneously formed on the upper level are back ear and front ear portions of the disposable product, which can be formed with methods and apparatus such as those disclosed in the simultaneously pending U.S. patent application Ser. No. 12/925,033, incorporated herein by reference, and described in the schematic as the "NOSE unit."

As disclosed therein, discrete preferably trapezoidal ear pieces are initially cut alternating between a correct orientation and an incorrect (reversed) orientation. The reversed ear is required to be rotated 180° into the correct orientation such that the ears and associated tape present a left ear and a right ear on the diaper.

To accomplish the reversal of the ear pattern, discrete ear pieces are picked up at the nested ear pitch by an ear turner assembly that will expand to a pitch large enough for ears to be unnested and allow clearance for every other ear to be rotated. The rotated ears are then unnested and into the correct orientation.

Two ear turner assemblies can be provided, to rotate every other ear applied to the right side of the product, and every other ear applied to the left side of the product. In this manner, for a single product, one of the two ears will have been rotated 180°.

Ear application to a chassis web can be by a bump method with intermittent adhesive applied to the chassis web, or can be by vacuum transfer.

Still on the upper level, a cuff portion of the diaper can be supplied from the upper level, the top sheet can be stored and unwound, an acquisition layer can be stored and unwound, and a non woven backsheet/poly laminate can be stored, formed and unwound. All of the stored materials on the upper level can be retrieved automatically and mechanically to restock as the rolls are used up. Eventually the upper level materials, which generally overly the floor level machinery, are supplied down to the floor level for use in the diaper manufacturing process.

Together on the floor level, the back ear, front ear, cuff (now including cuff elastic), top sheet, acquisition layer, and backsheet/poly laminate are preferably simultaneously placed and coupled together and coupled with the previously formed core. The web can undergo folding, extraction and trimming of excess material, and application of material to tighten the diaper about the waist. Eventually, the product is folded and packaged.

Figure 2:
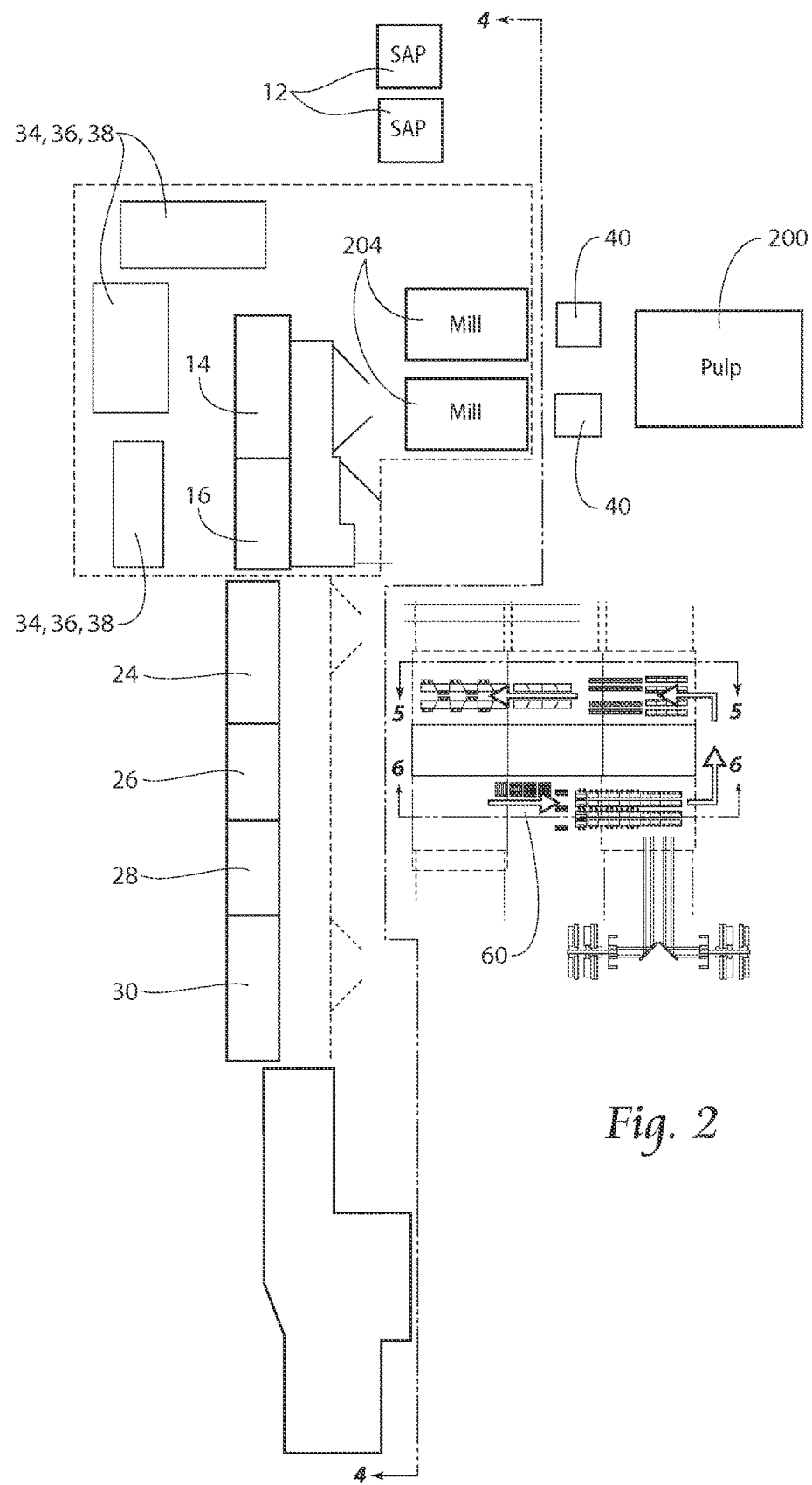
FIG. 2 is a top view of a floorplan layout of the web processing system of the present invention.
Figure 4:
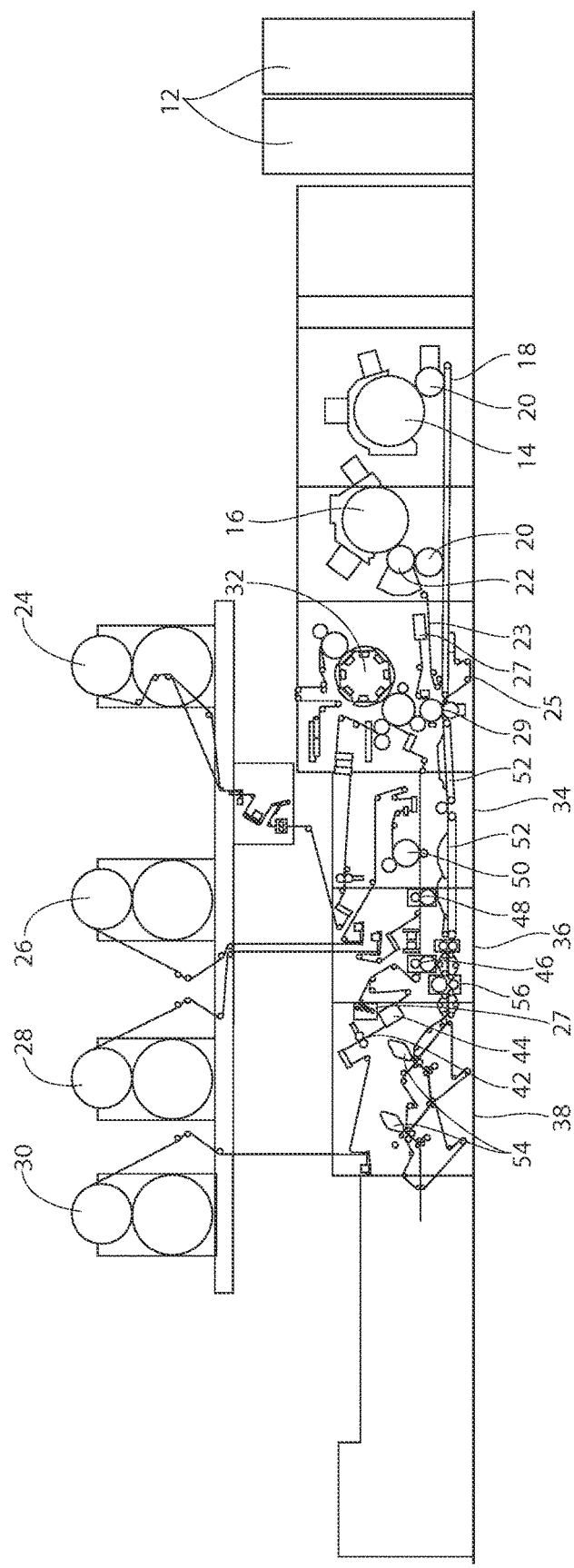
FIG. 4 is a side view of the ground level and mezzanine levels of the web processing system of the present invention.

Referring now to FIGS. 2 and 4, a preferred floor plan of the present invention is shown both from a top view (FIG. 2) and a side view (FIG. 4). As indicated, pulp rolls 200 feed raw pulp into a pulp mill 204, where the pulp is de-bonded. Super absorbent polymer is added from station 12. The SAP/pulp mixture, or pulp/SAP blend, or pulp and SAP is fed onto core forming drum 14. The pulp/SAP mixture is introduced to a core forming apparatus. Cores are made by conveying the pulp/SAP mixture through a duct and into a vacuum forming drum. Cores from core forming drum 14 are conveyed by conveyor 18 and core accelerator 20 downline. A secondary core forming drum 16 is likewise employed if a secondary core is desired, and the secondary core is passed through the debulking unit 22, and onto the core accelerator 20 and placed atop the primary core. A compression conveyor 23 keeps control of the core to pass it through to the introduction of poly laminate backsheet. A backsheet laminate is comprised preferably of a continuous nonwoven layer (for soft, cloth like feel), along with a moisture barrier layer, generally made from polypropylene or polyethylene film. This layer can be glued, ultrasonically bonded over the length of the backsheet, or applied as a patch with glue using a slip/cut process.

Figure 3:
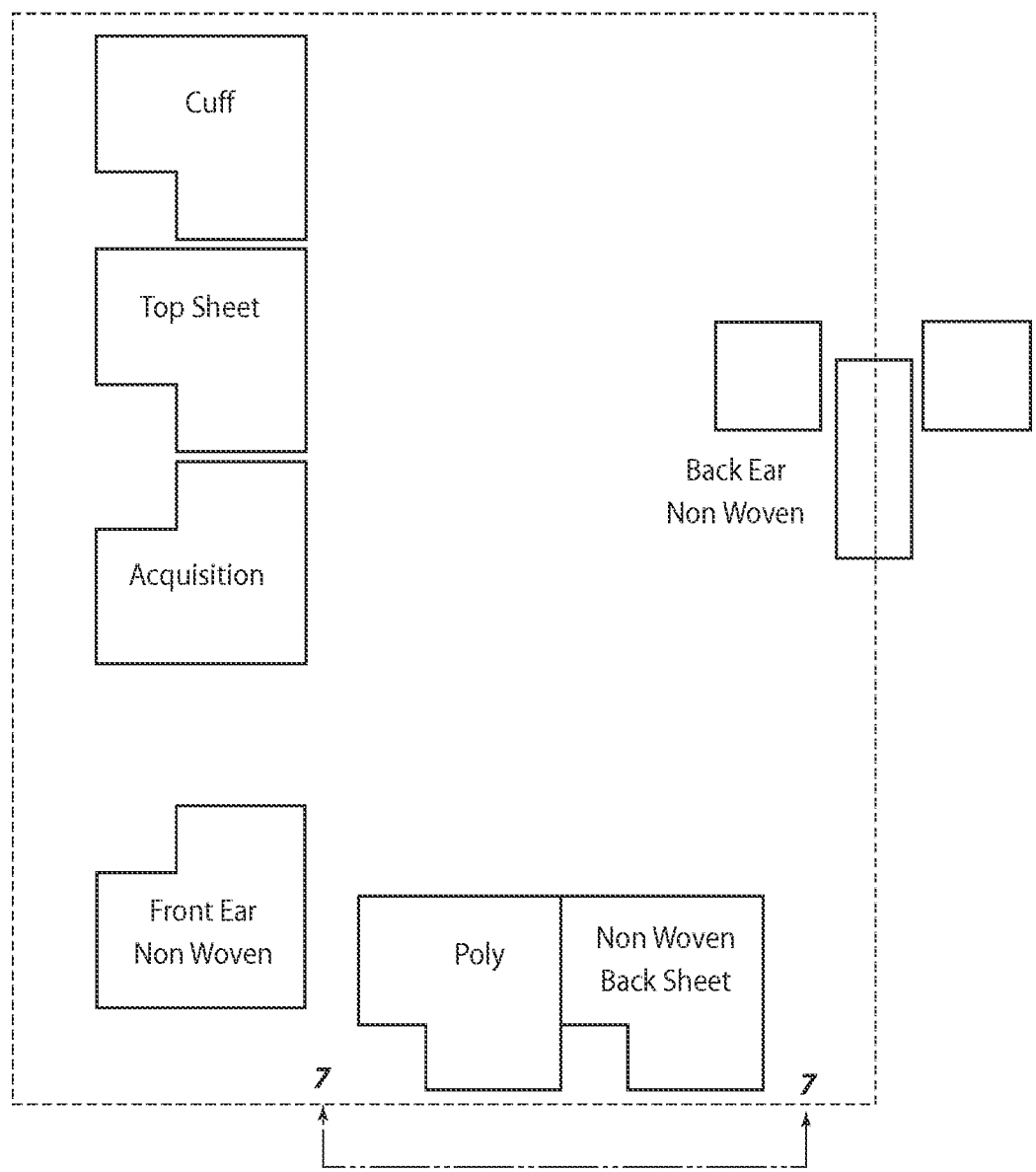
FIG. 3 is a top view of a floorplan layout of the web processing system of the present invention.
Figure 7:
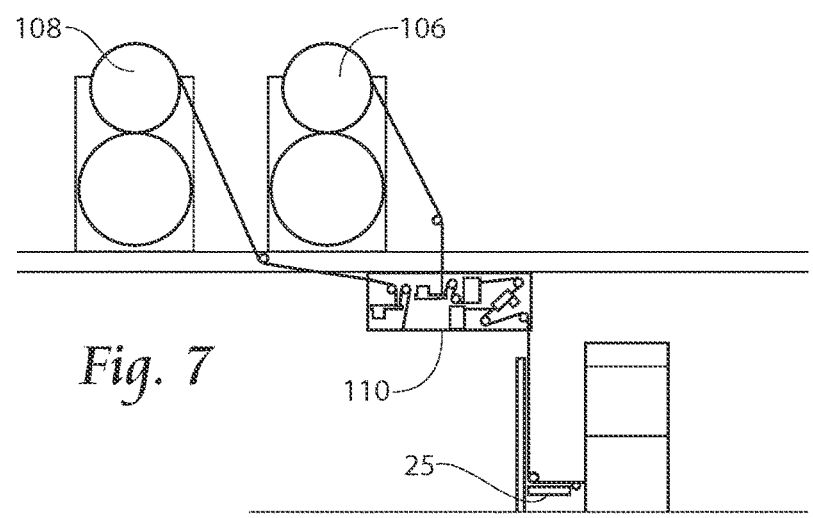
FIG. 7 is a side view of a soft backsheet lamination section of the present invention.

Referring to FIG. 7, the formation of the soft backsheet lamination is shown in side view. A nonwoven backsheet roll is carried on the upper level along with its backup roll to be spliced in as inventories deplete (see FIG. 3) and laminated together at station 110.

Referring to FIGS. 4 and 7, it can be seen that a process interface module 110 is carried between said unwind level and said main processing level, said main level containing splice preparation equipment 110 located between the unwind level and the main process system level, for instance by hanging a process interface module 110 from a supplied I-beam. The process interface module can achieve many functions, such as slitting, laminating, and splice preparation. After being transported vertically, the poly laminated backsheet is introduced to the fed from the bottom, at station 25 (see FIGS. 3, 7). A nonwoven topsheet assembly, including a lycra and cuff portion and an absorbent distribution layer, enters the system prior to the boundary compression unit. Still referring to FIG. 3, it is noted that actual raw materials and the locations of those materials could vary in floor plan, but it is preferred that the materials remain on the vertical levels shown.

Referring back to FIG. 4, this poly laminate and core combination is passed to boundary compression unit 29. It is at unit 29 that other diaper elements are introduced in pre-formed fashion, from the upper level components on FIG. 1B. Also, lycra unwind unit 27 introduces lycra, in addition to the pre-formed upper level diaper components, at this point.

Referring to FIG. 2, the upper level components comprise the front ear non-woven supply unit 24, to supply the front ears, the acquisition layer provided from unwind unit 26, the top sheet supplied from the supply and unwind station 28, and the cuff components supplied from the cuff supply unit 30 to supply the cuff material for lower level slitting/spreading and introduction of lycra, and foldover of the lycra to form the cuff. These materials are fed in the pathways shown, and introduced to the boundary compression unit 29, in the sequence shown in FIGS. 1A and 1B.

Figure 5:
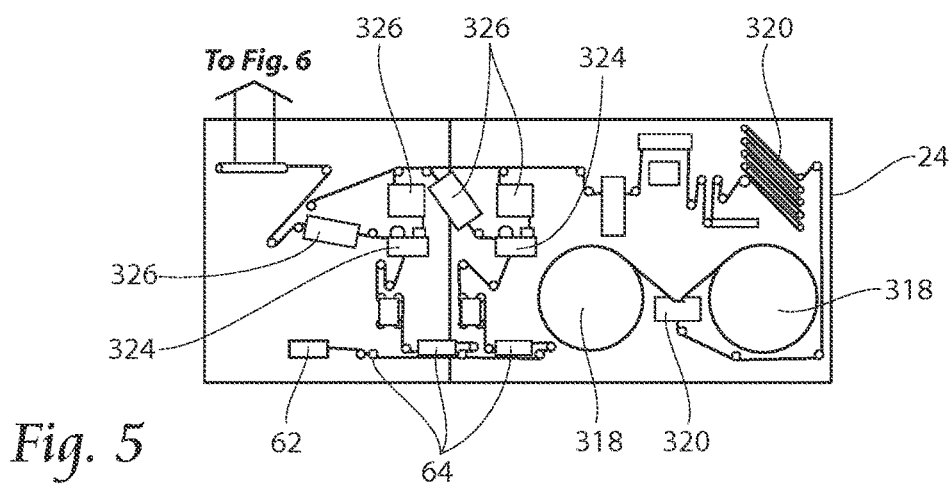
FIG. 5 is a side view of an extension panel construction section of the present invention.
Figure 6:
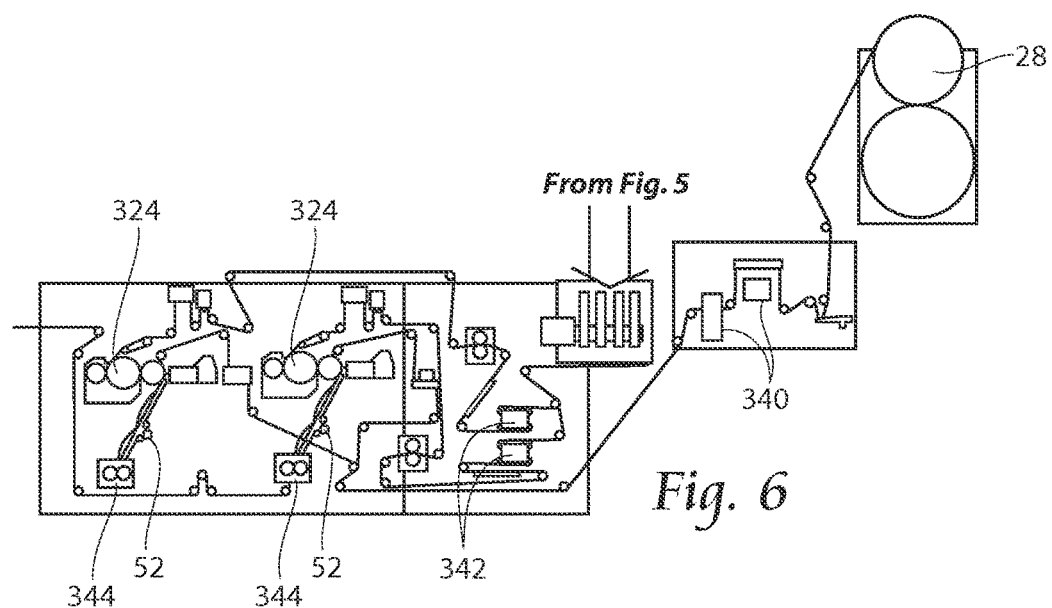
FIG. 6 is a side view of a back ear final construction section of the present invention.

Still referring to FIG. 2, on the upper level, the back ear and extension panel are formed at station 60. The back ear section is formed as shown in FIG. 6, using the methods and apparatus formed in U.S. application Ser. No. 12/925,033, disclosed herein by reference. The extension panel section is formed as shown in FIG. 5. In particular, the depiction and description shown in FIG. 19A-26 of U.S. application Ser. No. 12/925,033 results in the back ear/extension panel formation depicted in FIGS. 5 and 6. Ultimately the back ear/extension panel construction is transported as depicted, downwards toward the nested zero waste ear rotation unit 27 as shown on FIG. 4, also described in detail in U.S. application Ser. No. 12/925,033, for instance at FIG. 8A.

Still referring to FIG. 4, front ears are formed at unit 24 using preferably non-woven material, and are placed onto the chassis web preferably by slip-cut technique after being conveyed circuitously and downwardly towards the boundary compression unit 29.

Cuff unit 30 conveys, from the upper level, cuff material to the lower level where right and left cuffs are formed by passing the cuff material irst through slitter 42, spreader 44. Lycra unwind unit 27 feeds strands of lycra onto the cuff material, and then a bonding/foldover unit 46 seals the lycra strands within a foldover portion of the non-woven material to create the cuff.

An additional bonding unit 48 couples the previously created cuff with the incoming topsheet material 28, fed from the upper level downwardly. The cuff/topsheet combination is fed toward incoming acquisition layer 26 for acquisition placement at station 50 and that combination is then fed toward the NOSE unit 32, where the previously formed materials will be joined with the cuff/topsheet/acquisition combination. After the NOSE unit, all of the materials are then joined at the boundary compression unit, including the nonwoven topsheet assembly, including a absorbent distribution layer, lycra and cuff portion, which have entered the system prior to the boundary compression unit.

Now moving right to left on FIG. 4, the formed diaper can be subjected to folding plows 52 to fold over front ear and back ear/extension panels, passed through a die cut unit 56 to sever individual products from the previously continuous web, and then past tucker blades 54 to fold the products at the crotch region or elsewhere desired for packaging and bagging operations at station 00.

Referring now to FIG. 5, the extension panel construction is shown. The formation of side panel assemblies begins with an non-woven web material 318, supplied in primary and backup roll fashion, with splicer 320 and accumulator 322 used to provide a continuous web, which is slit and spread into discrete non-woven web portions (see FIG. 2), each of the non-woven web portions also preferably being cut in the cross-machine direction into the preferred size.

To each of the discrete non-woven web portions, one or more fastening mechanisms are applied. Fastening mechanisms can be tape tabs, covered tape tabs, strips of hook and loop material, continuous hook and loop material, patches of hook and loop material, etc. The fastening mechanisms will be unfastened and refastened about the waist of the user to tighten the disposable garment about the waist.

The fastening mechanisms are supplied by incoming web 62, slit and spread by units 64 and applied via slip cut unit 324 onto the non-woven 318.

Next, the non-woven webs 318 carrying fastening mechanisms 322 are folded over, creating a folded web 318 and folded-over fastening mechanisms. This causes the combination of the non-woven web 318 and the fastening mechanisms to be narrower than the discrete non-woven web portions. It is noted that the folded fastening mechanisms of web portions 318*a* and 318*b* will have opposing fastening mechanisms 322' as they will become the right and left hip waist fastening mechanisms, respectively, once placed about the waist of a user (shown later in the process).

Referring now to FIG. 6, the back ear final construction is shown, a cross sectional view of the designated view of FIG. 2. This process is disclosed, e.g., in FIGS. 20-22 of simultaneously pending U.S. patent application Ser. No. 12/925, 033, incorporated herein by reference.

The back ear final construction receives where indicated the partially completed extension panel assembly where indicated, which first pass through additional folding units 342. A back ear web 28 is provided upon which to attach the previously formed extension panel. This too can be slit and spread into discrete stretch laminate web portions.

Next, the non-woven web portions, including their respective fastening mechanisms, are slip/cut and bonded to stretch laminate web portions in a staggered relationship, forming the side panel assemblies in four different lanes. The non-woven web portions can be bonded to the stretch laminate web portions in any fashion, such as by ultrasonic bonding.

The stretch laminate portions can also be folded if desired, or the stretch laminate portions in combination with the non-woven web portions can all be folded together and again, by plows 52. The back ear/extension panel construction assembly is then conveyed to the floor level NOSE unit 32, ultimately for placement with the other components and the boundary compression unit 29.

Figure 8:
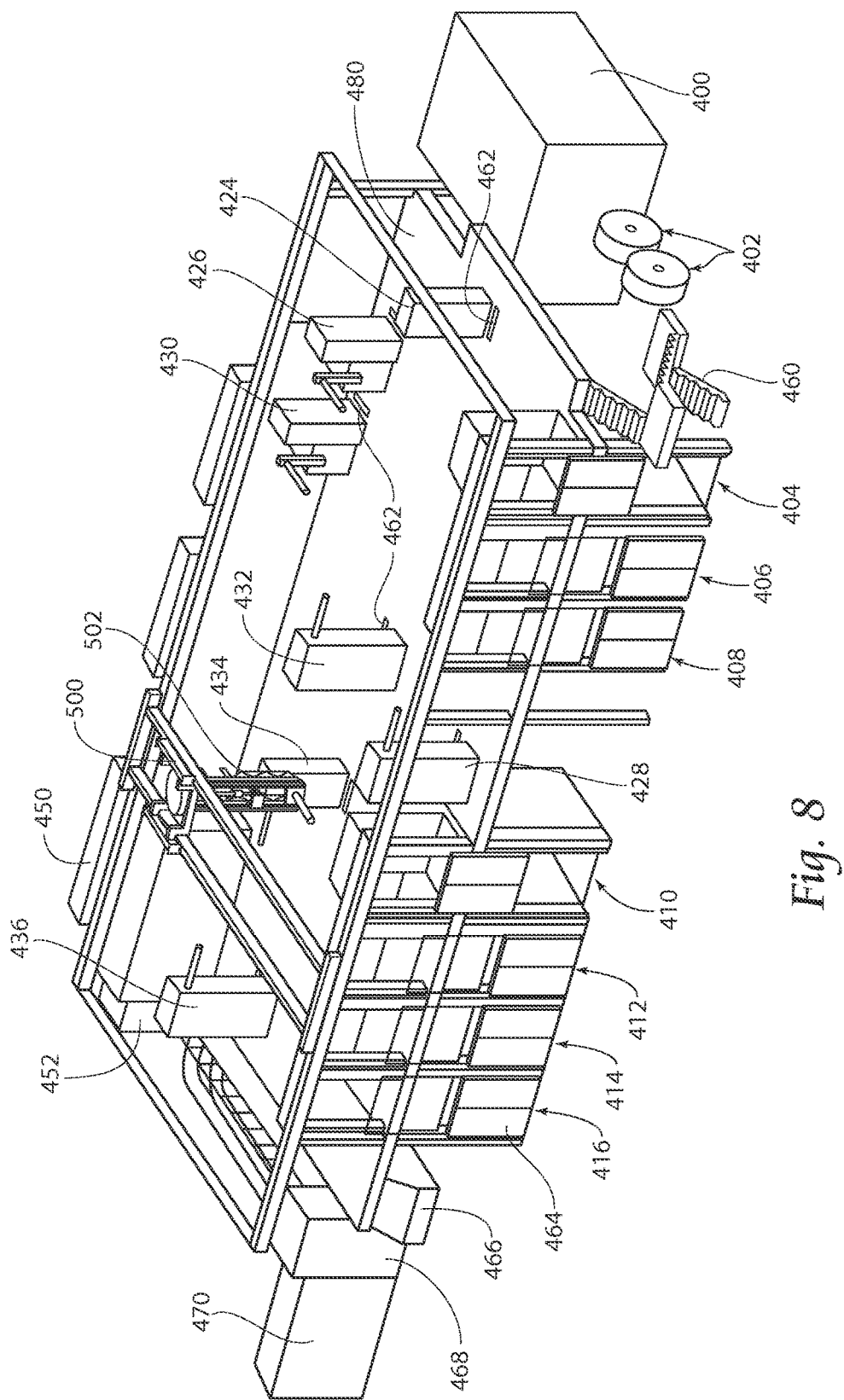
FIG. 8 is a perspective view of a mezzanine and floor level of a web processing system of the present invention used to create a pant-type product.

Referring now to FIG. 8, a perspective view of a mezzanine (or material unwinding) level 480 and floor (or main processing) level 482 of a web processing system used to create a pant-type product of the present invention is shown. The material unwinding level 480 is a human-free zone, intended for no human occupation during machine operation in areas accessible by a gantry crane 500.

On the floor level, a series of ground floor material access doors 464 are provided. These access doors 464 are each preferably dedicated to a single material. For example in a preferred embodiment, door address 416 is for transporting inner non-woven material from the ground level to the mezzanine level. Address 414 is for outer non-woven, address 412 for non-woven backsheet material, address 410 for non-woven topsheet material, address 408 for poly backsheet material, address 406 for acquisition layer material, and address 404 for tissue material. A vertical reciprocating conveyor (VRC) operates behind each access door 464 to lift a full rack of waiting new material rolls (FIG. 10) supplied into the addresses in magazines to the mezzanine level. Alternatively, descending robots can be used in place of the VRCs.

Preferably, when an access door 464 is open, a corresponding access door on the mezzanine level is closed, and vice versa.

On the material unwinding level 480, unmanned, auto-fed material unwinding systems are provided corresponding to the materials supplied to addresses above. In a preferred layout, turret unwind 424 is for a tissue unwind, corresponding to address 404 on the ground and mezzanine levels (turret unwind detail provided in FIG. 13). An acquisition layer unwind station 426 (corresponding to station 406) is provided, as are turret unwinds for poly backsheet unwind 428 (corresponding to station 408), non-woven topsheet layer 430 (corresponding to station 410), non-woven backsheet layer 422 (corresponding to station 412), outer chassis non-woven unwind 434 (corresponding to station 414), and inner chassis nonwoven unwind 436 (corresponding to station 416).

As material is unwound from the unwinds 424, 426, 428, 430, 432, 434, and 436, material is fed through material supply slots 462 in the floor of the mezzanine level, downward to the ground level 482. There, the materials are fed into and used by the system, as shown in FIGS. 1A and 1B, 2, and 4-7.

Figure 13:
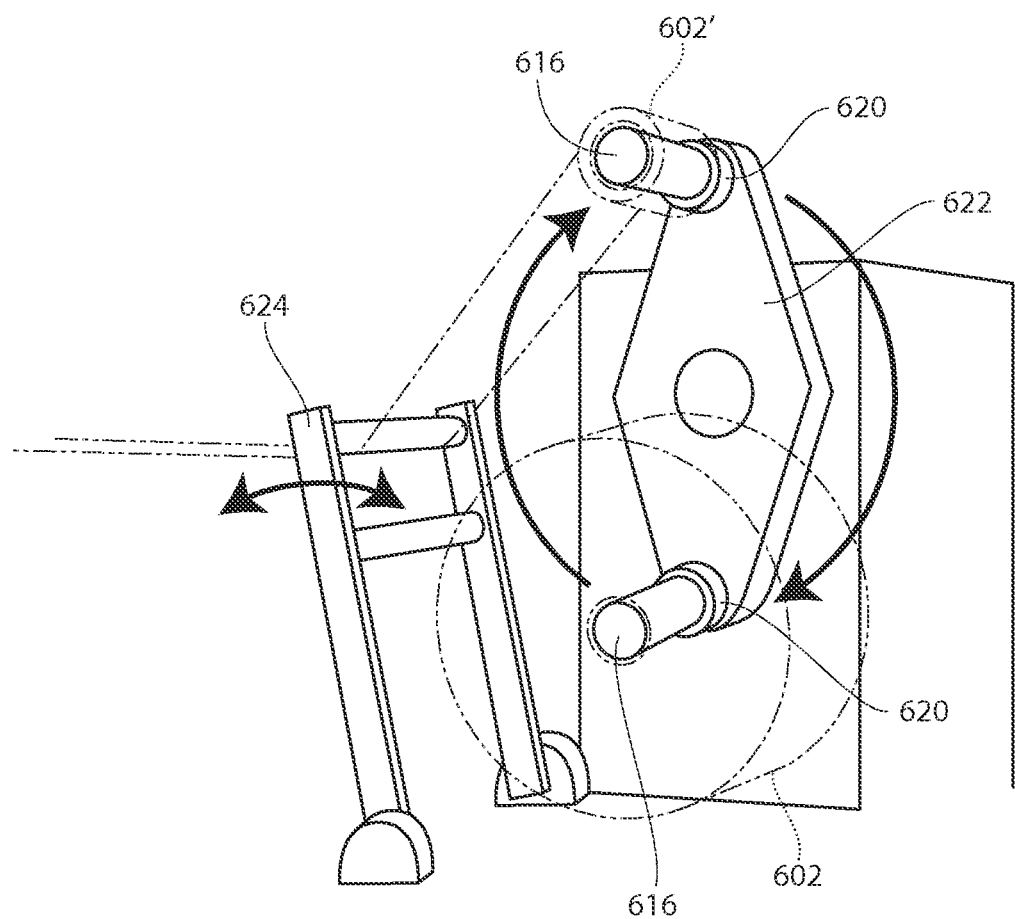
FIG. 13 is a side view of a turret unwind and splicing system for carrying expiring material rolls and waiting new material rolls.

As a connected material roll feeds material from the mezzanine level through an opening 462 in the floor of the mezzanine level to the floor level, the material roll will eventually expire. Referring now to FIG. 13, a side view of a turret unwind and splicing system for carrying expiring material rolls and waiting new material rolls is shown.

Turret unwinds are described for exemplary purposes in U.S. Pat. Nos. 6,701,992, 3,655,143, 3,306,546, 3,460,775, which are incorporated herein by reference.

Still referring to FIG. 13, when the system detects that one of the expiring material rolls 602' in the top position on unwinds 424, 426, 428, 430, 432, 434, and 436 is set to expire, a splice sequence is initiated between the expiring material roll 602' and the waiting new material roll 602. In a preferable embodiment, a running or expiring roll 602' is at a top position of the turret unwind of FIG. 13, with a waiting new material roll 602 placed by the gantry crane system located at a bottom position of the turret unwind on shaft 616. When it is detected that the running roll is coming close to expiration, the waiting new material roll 602 is driven up to a surface speed of expiring roll. A hot wire splicer arm 624 moves in adjacent to the waiting new material roll, brings in the running web into close proximity to the waiting new material roll 602. At the moment of splice, the hot wire arm 624 bumps the expiring web 602' to the waiting new material roll, and at the precise moment of contact, a splice tape is introduced to splice the waiting new material roll 602 and the expiring roll 602' together, and at the same time as the bump, the hot wire arm 624 severs the running web with a hot wire. In this manner, the expiring web is instantly taped to the leading edge of the new roll.

Next, the rotating turret arm 622 rotates clockwise to place the waiting new material roll 602 into the expiring roll position 602'. A kicker ring 620 next bumps the remainder of the previously expiring roll 602' off of shaft 616 for discard.

Next, the system demands a replacement waiting new material roll to place upon the shaft 616 at the bottom position of the turret unwind.

At the mezzanine level addresses 404, 406, 408, 410, 412, 414, and 416, magazines of waiting new material roll (FIG. 10) are received from the ground level, and wait for demand. The gantry crane 500 is summoned to pick up a material roll from a cart (FIG. 10) stationed at the dedicated VRC stations, and transport the full material roll to a turret unwind system dedicated to that particular material. The system detects which waiting new material roll requires replacement after its predecessor has been spliced and turned into an expiring roll, and then travels the crane/robot combination 500/502 to the appropriate mezzanine level address 404, 406, 408, 410, 412, 414, and 416 and obtains a replacement waiting new material roll.

The gantry robot is programmed to discard the remainder of the expiring roll into a waste chute (not shown) on the mezzanine level, and then to obtain a replacement waiting new material roll from the dedicated VRC from which the appropriate material is located on the cart. When the system detects that all rolls of waiting new material roll are used from a supply cart (FIG. 10), the VRC containing the empty cart is automatically transported to the floor level for replacement of all of the waiting new material rolls.

During machine operation, those portions of the mezzanine level accessible by a gantry crane system 500 are designed to operate without human occupation. This not only provides an added measure of safety, but an added measure of automation for the machine. A gantry crane system 500 operates robotically on an overhead system that allows movement across a horizontal plane. The present invention uses the gantry crane 500 for horizontal movement, and a robotic arm 502 capable of vertical movement and rotation, and equipped with a camera operated location system (see FIGS. 11 and 12) to detect the position of the core of waiting new material rolls for pickup, and to deposit precisely a core of a replacement waiting new material roll onto arms of turret unwinds for use in the system.

Gantry robots 500 are preferred for this pick and place applications because of positioning accuracy, aided by vision systems. Positional programming is done in reference to an X, Y, Z coordinate system.

Although humans can access the mezzanine level 480 by stairs 460 for equipment service, no human occupation during operation is intended. Humans can also access the mezzanine level 480 behind access door 452, this portion of the mezzanine level 480 is physically separated from the human-free zone of the other portions of the mezzanine level 480. Access door 452 is used to access physically divided power station and control station 450. This station is for control panels, ultrasonic bonder control, and drive controls.

Also evident on FIG. 8 are pulp rolls 402 supplying pump mill 400 at the beginning of the processing on the main floor, and a final knife unit 466, an ear folding and horizontal pad turner 468, and lastly a cross-folder 470 which discharges the diapers to product packaging downstream.

This unique machine layout has achieved significant machine length decrease. Exemplary prior art diaper making machines for a pant process are approximately 44 meters, and this new machine layout can be achieved in less than 34 meters, a 23% shorter overall machine length from the beginning of the pulp unwind to the end of cross-folder 470. A range of 20-35% decrease in machine length can be achieved.

Figure 9:
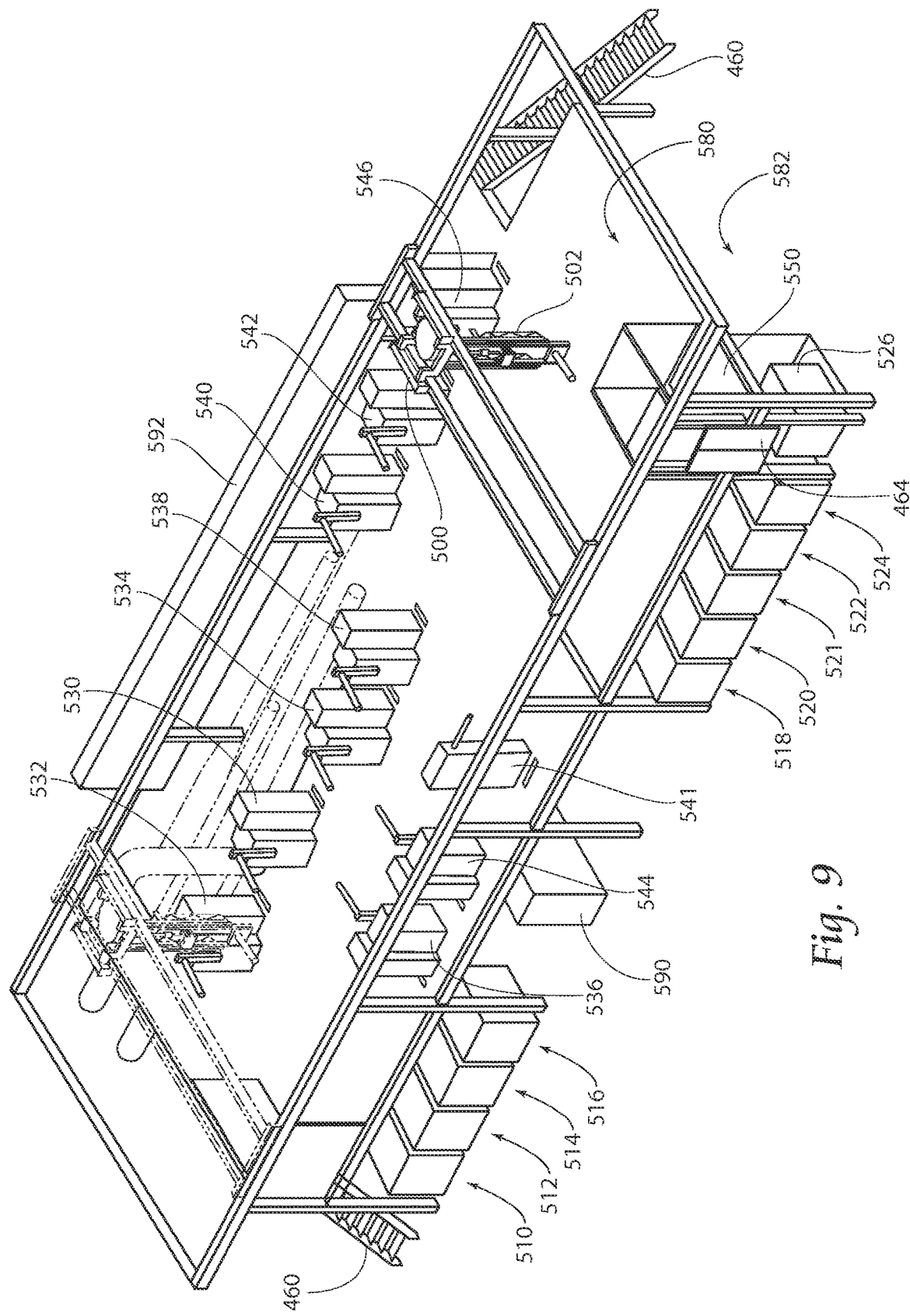
FIG. 9 is a perspective view of an alternate mezzanine and floor level of a web processing system of the present invention used to create a brief-type product.

Referring now to FIG. 9, a perspective view of an alternate mezzanine and floor level of a web processing system of the present invention used to create a brief-type product is shown.

In this embodiment, carts of materials are staged initially on the ground floor. In an exemplary embodiment, loading carts are position at stations 510 (upper tissue), 512 (lower tissue), 514 (poly backsheet), 516 (non-woven backsheet), 518 (back ear), 520 (acquisition layer), 521 (front ear), 522 (non-woven topsheet), 524 (extension panel), and 526 (cuff). These materials are transported to and placed behind VRC door 464 and transported by VRC 550 to the mezzanine level 480. A similar demand/replacement system is employed in the brief-type product floor layout as in the pant-type product layout described in FIG. 8. Namely, expiring materials are fed through slots in the floor of the mezzanine level, a splicing sequence is initiated, and a material replacement sequence is initiated, whereby a material roll is acquired by crane/robot combination 500/502 and transported to and placed on the turret unwind systems.

In the pictured embodiment, a lower tissue turret unwind 532 is provided as are turret unwind stations for upper tissue (530), poly backsheet (534), non-woven backsheet (536), back ear (538), acquisition layer (540), front ear (541), inner top-sheet non-woven extension panel (544), cuff (546). These materials are all fed downward to be used in a brief-type diaper.

This unique machine layout has achieved significant machine length decrease. Exemplary prior art diaper making machines for a brief process are approximately 41 meters, and this new machine layout can be achieved in less than 29 meters, a 30% shorter overall machine length from the beginning of the pulp unwind to the end of cross-folder 470. A range of 20-35% decrease in machine length can be achieved. A power station and control station 592 is provided. Additionally, certain components can be fed at the ground level, for instance an offline stretch material unwind 590.

Figure 10:
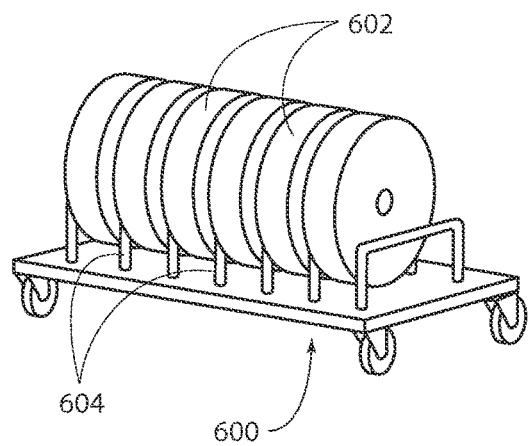
FIG. 10 is a perspective view of a loaded material roll supply cart of the present invention.

Referring now to FIG. 10, a perspective view of a loaded material roll supply cart 600 or magazine of the present invention is shown. A material staging magazine 600 is provided to carry waiting new material rolls 602 from a ground level to a mezzanine level 480, the mezzanine level 480 carrying a series of turret unwind systems for dispensing materials from the mezzanine level back to the ground level. The material staging magazines 600 contain a series of individual roll stabilization features 604 which prevent waiting new material rolls 604 from tipping during material transport and unloading. The cart 600 is filled on the ground level, and rolled into the appropriate ground level addresses 404, 406, 408, 410, 412, 414, and 416, for transport to mezzanine level addresses 404, 406, 408, 410, 412, 414, and 416. The rolls are then summoned as described above.

Figure 11:
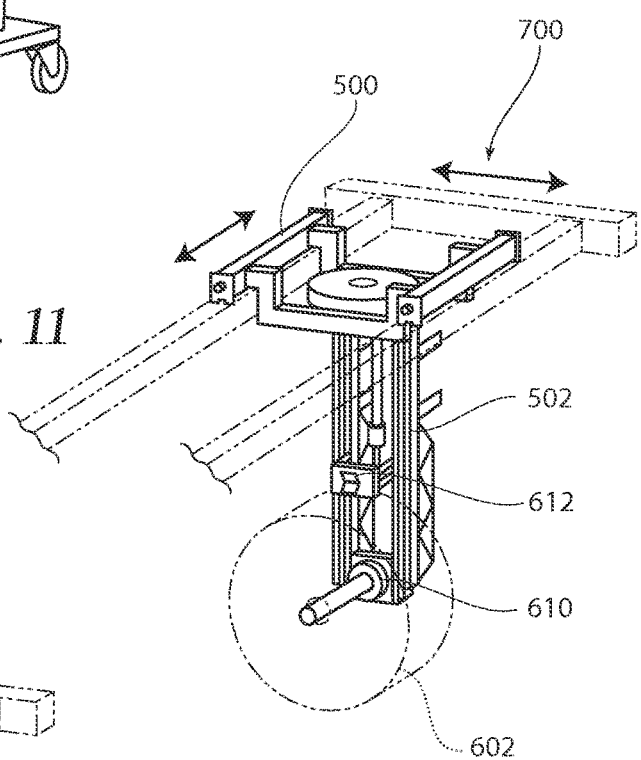
FIG. 11 is a perspective view of a gantry crane system carrying a material roll used in the present invention, shown in a retracted position.

Referring now to FIG. 11, a perspective view of a roll transfer device 700 comprising a gantry crane 500 system carrying a material roll 602 used in the present invention is shown in a retracted position. A camera 612 is used to detect the position of a core of a waiting new material roll during pickup of a waiting new material roll by the robot off of a cart 600, and also to detect the position of the shaft 616 on the turret unwind systems (FIG. 13) upon which to push the material roll 602 with roll bumper 610. Lasers, radar, or ultrasonics can also be used to measure distance and position, either in addition to or instead of camera 612.

Figure 12:
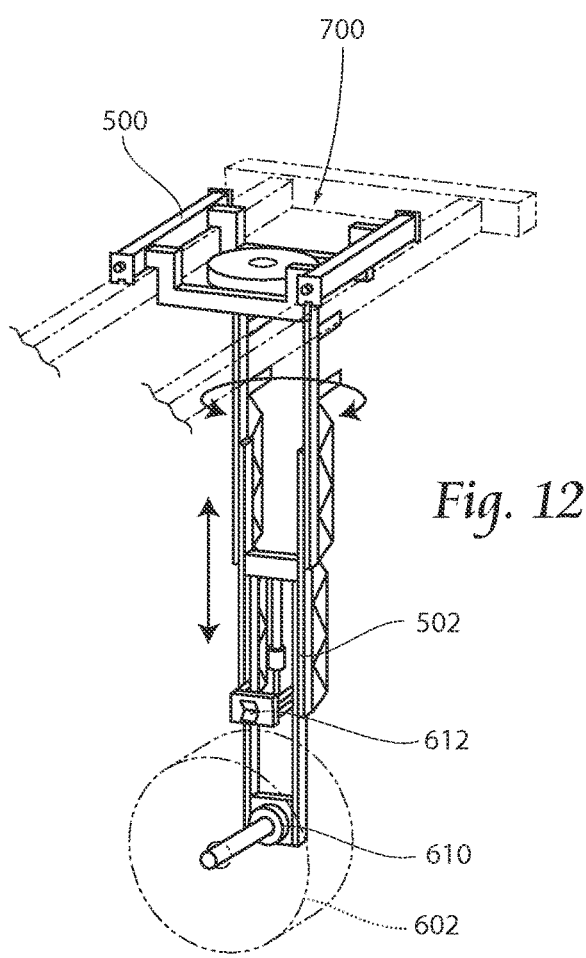
FIG. 12 is a perspective view of a gantry crane system carrying a material roll used in the present invention, shown in an extended position.

FIG. 12 is a perspective view of a gantry crane 500 carrying a material roll 602 used in the present invention, the robotic arm 502 shown in an extended position.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A multi-level machine for manufacturing disposable products, the machine comprising a main processing lower floor level for manufacturing a disposable product and a material unwinding upper floor level, said material unwinding level carrying unmanned, auto-fed material unwinding systems comprising a plurality of turret systems, said turret systems carrying an expiring roll of material and a standby roll of material selectively coupled to said expiring roll of material, said auto-fed material unwinding systems operatively connected to said expiring roll of material at said material unwinding level and said auto-fed material unwinding systems feeding the materials vertically through material supply openings in a floor of the material unwinding upper floor level to the main processing lower floor level, said main processing lower floor level comprising a manufacturing station for manufacturing a disposable product, said waiting new material rolls staged at material addresses corresponding to at least one of said turret systems, said turret systems in communication with a system for retrieving and transporting said waiting new material roll from said material address to said turret system, said turret system receiving a roll from said system for retrieving and transporting said waiting new material roll from said material address to said turret system.

2. A machine according to claim 1, wherein said unwinding level is supplied with waiting new material rolls comprising at least one of an inner non-woven material, an outer-non-woven material, a non-woven backsheet material, a non-woven topsheet material, a poly backsheet material, an acquisition layer material, and a tissue layer.

3. A machine according to claim 2, wherein a vertical reciprocating conveyor carries said waiting new material rolls from said main processing level to said material unwinding level.

4. A machine according to claim 2, wherein a robotic system carries said waiting new material rolls from said main processing level to said material unwinding level.

5. A machine according to claim 2, wherein said waiting new material rolls are staged on said material unwinding level at said material addresses dedicated to at least one of said materials.

6. A machine according to claim 1, said machine further comprising material unwinding systems on said main processing level.

7. A machine according to claim 1, said machine further comprising a plurality of roll staging magazines for storing waiting new material rolls before transporting said waiting new material rolls from said main processing level to said material unwinding level.

8. A machine according to claim 1, wherein said materials are staged at material addresses on said material unwinding level, said material addresses dedicated to each of said materials, said machine further comprising a robotic assembly to acquire at least one material roll from one of said material addresses and to transport and place said at least material roll onto one of said auto-fed material unwinding systems.

* * * * *